US008343938B2

(12) United States Patent
Peschle et al.

(10) Patent No.: US 8,343,938 B2
(45) Date of Patent: Jan. 1, 2013

(54) USES AND COMPOSITIONS COMPRISING MIRNAS

(75) Inventors: Cesare Peschle, Rome (IT); Gianluigi Condorelli, Rome (IT)

(73) Assignee: Consiglio Nazionale delle Ricerche, Rome (IT)

( * ) Notice: Subject to any disclaimer, the term of this patent is extended or adjusted under 35 U.S.C. 154(b) by 241 days.

(21) Appl. No.: 12/376,395

(22) PCT Filed: Aug. 3, 2007

(86) PCT No.: PCT/EP2007/007131
§ 371 (c)(1),
(2), (4) Date: Aug. 11, 2010

(87) PCT Pub. No.: WO2008/015028
PCT Pub. Date: Feb. 7, 2008

(65) Prior Publication Data
US 2011/0184048 A1 Jul. 28, 2011

(30) Foreign Application Priority Data
Aug. 4, 2006 (GB) .................................. 0615609.5

(51) Int. Cl.
C12N 15/11 (2006.01)
A61K 48/00 (2006.01)
C07H 21/02 (2006.01)
C07H 21/04 (2006.01)

(52) U.S. Cl. ..................................... 514/44 A; 536/24.5

(58) Field of Classification Search .................... 514/44; 536/23.1, 24.3, 24.33
See application file for complete search history.

(56) References Cited

U.S. PATENT DOCUMENTS
7,683,036 B2 * 3/2010 Esau et al. .................. 514/44 R
2006/0246491 A1 11/2006 Srivastava FOREIGN PATENT DOCUMENTS
WO WO 2006/107826 10/2006
WO WO 2007/070483 6/2007
WO WO 2008/015028 2/2008

OTHER PUBLICATIONS

Maha Abdellatif (Circulation Research, 2010 vol. 106:16-18).*
See Carè et al. (Nature Medicine, 2007 vol. 13:613-618).*
Bartel, D.P. (Jan. 23, 2004) "MicroRNAs: Genomics, Biogenesis, Mechanism, and Function," *Cell* 116:281-97.
Bergemann et al. (Mar. 2005) "The Etiology of Wolf-Hirschhorn Syndrome," *Trends Genet.* 21(3):188-195.
Brown et al. (May 2006) "Endogenous MicroRNA Regulation Suppresses Transgene Expression in Hematopoietic Lineages and Enables Stable Gene Transfer," *Nat. Med.* 12(5):585-591.
Chen et al. (Jan. 2, 2004) "MicroRNAs Modulate Hematopoietic Lineage Differentiation," *Science* 303:83-86.
Chen et al. (Feb. 2006) "The Role of MicroRNA-1 and MicroRNA-133 in Skeletal Muscle Proliferation and Differentiation," *Nat. Genet.* 38(2):228-233 Plus Supplementary Information.

(Continued)

*Primary Examiner* — Terra Cotta Gibbs
(74) *Attorney, Agent, or Firm* — Greenlee Sullivan P.C.

(57) ABSTRACT

The cardiac-specific miRs, miR-133 and miR-1, are critical in determining hypertrophy of cardiac myocyte cells (CMC), and that restoration of levels of expression thereof can alleviate the symptoms of CMC hypertrophy.

10 Claims, 12 Drawing Sheets

OTHER PUBLICATIONS

Figure 1:
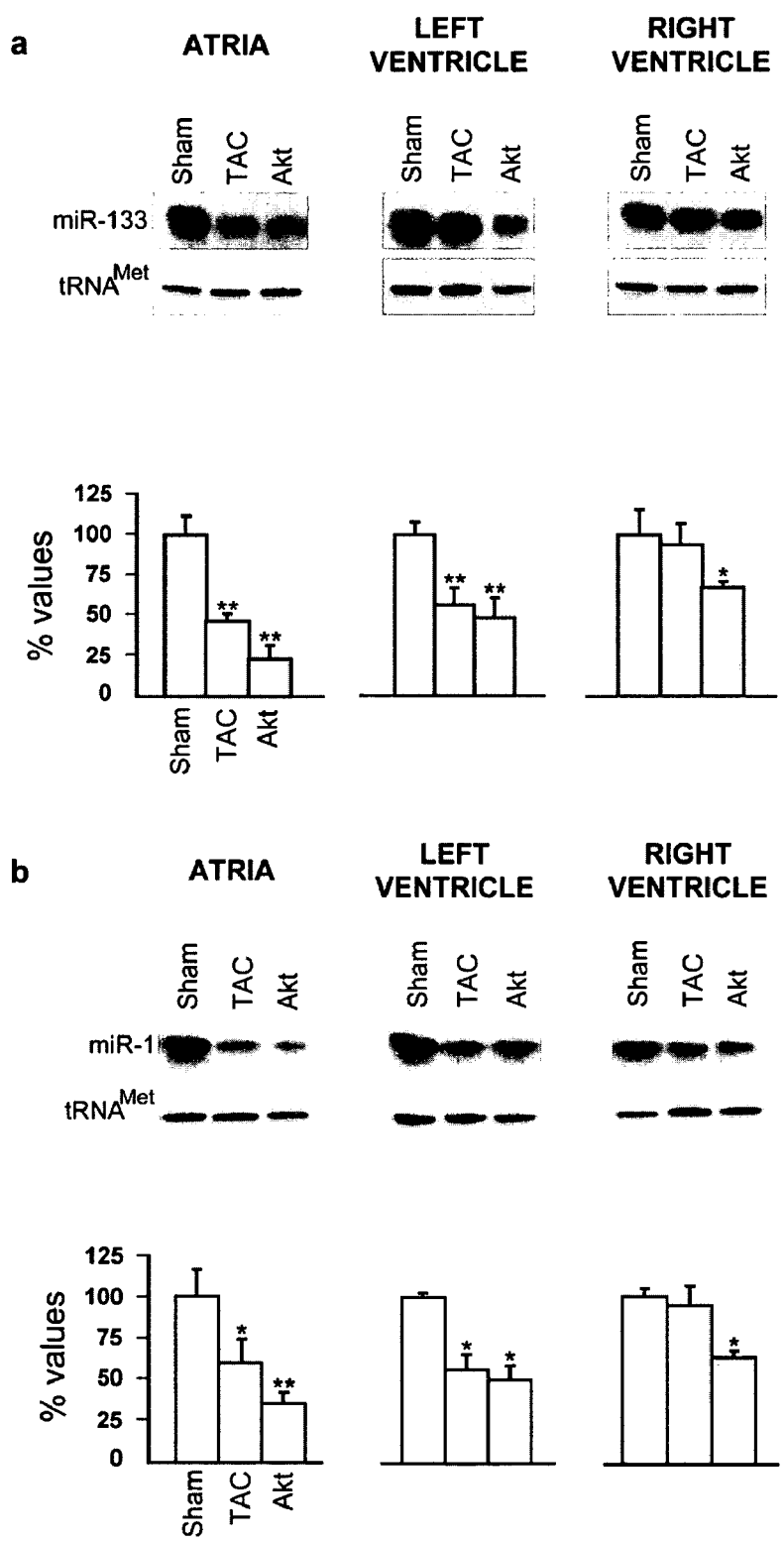

Cheng et al. (2005) "Antisense Inhibition of Human miRNAs and Indications for an Involvement of miRNA in Cell Growth and Apoptosis," *Nuc. Acids Res.* 33(4):1290-1297.

Clerk et al. (May 26, 2000) "Small Guanine Nucleotide-Binding Proteins and Myocardial Hypertrophy," *Circ. Res.* 86:1019-1023.

Condorelli et al. (Sep. 17, 2002) "Akt Induces Enhanced Myocardial Contractility and Cell Size in Vivo in Transgenic Mice," *Proc. Nat. Acad. Sci. USA* 99(19):12333-12338.

Dorn et al. (Jun. 13, 2003) "Phenotyping Hypertrophy: Eschew Obfuscation," *Circ. Res.* 92:1171-1175.

Dresios et al. (Feb. 8, 2005) "Cold Stress-Induced Protein Rbm3 Binds 60S Ribosomal Subunits, Alters MicroRNA Levels, and Enhances Global Protein Synthesis," *Proc. Nat. Acad. Sci. USA* 102(6):1865-1870.

Esquela-Kerscher et al. (Apr. 2006) "Oncomirs-microRNAs with a Role in Cancer," *Nature Rev. Cancer* 6:259-269.

Felli et al. (Dec. 13, 2005) "MicroRNAs 221 and 222 Inhibit Normal Erythropoiesis and Erythroleukemic Cell Growth via Kit Receptor Down-Modulation," *Proc. Nat. Acad. Sci. USA* 102(50):18081-18086.

Houbaviy et al. (Aug. 2003) "Embryonic Stem Cell-Specific MicroRNAs," *Dev. Cell.* 5:351-358.

International Preliminary Report on Patentability, Corresponding to International Application No. PCT/EP2007/007131, Mailed Feb. 19, 2009.

Iwatate et al. (2003) "In Vivo High-Efficiency Transcoronary Gene Delivery and Cer-LoxP Gene Switching in the Adult Mouse Heart," *Gene Ther.* 10:1814-1820.

John et al. (Nov. 2004) "Human MicroRNA Targets," *PLoS Biol.* 2(11):1862-1879(e363).

Krek et al. (May 2005) "Combinatorial MicroRNA Target Predictions," *Nat. Genet.* 37(5):495-500.

Krutzfeldt et al. (Dec. 1, 2005) "Silencing of MicroRNAs in Vivo with Antagomirs," *Nature* 438:685-689.

Kwon et al. (Dec. 25, 2005) "MicroRNA1 Influences Cardiac Differentiation in Drosophila and Regulates Notch Signalling," *Proc. Nat. Acad. Sci. USA* 102(52):18986-18991.

Lagos-Quintana et al. (Oct. 26, 2001) "Identification of Novel Genes Coding for Small Expressed RNAs," *Science* 294:853-858.

Lagos-Quintana et al. (2003) "New MicroRNA from Mouse and Human," *RNA* 9(2):175-179.

Latronico et al. (2004) "Regulation of Cell Size and Contractile Function by AKT in Cardiomyocytes," *Ann. NY Acad. Sci.* 1015:250-260.

Lim et al. (Mar. 7, 2003) "Vertebrate MicroRNA Genes," *Science* 299:1540.

Liu et al. (Jun. 29, 2004) "An Oligonucleotide Microchip for Genome-Wide MicroRNA Profiling in Human and Mouse Tissues," *Proc. Nat. Acad. Sci. USA* 101(26):9740-9744.

McKinsey et al. (Mar. 2005) "Toward Transcriptional Therapies for the Failing Heart: Chemical Screens to Modulate Genes," *J. Clin. Invest.* 115(3):538-546.

Nagai et al. (2003) "Cdc42 Plays a Critical Role in Assembly of Sarcomere Units in Series of Cardiac Myocytes," *Biochem. Biophys. Res. Commun.* 305:806-810.

Pei et al. (Feb. 28, 2003) "Interactions Between Fission Yeast Cdk9, its Cyclin Partner Pch1, and mRNA Capping Enzyme Pct1 Suggest an Elongation Checkpoint for mRNA Quality Control," *J. Biol. Chem.* 278(9):7180-7188.

Poy et al. (Nov. 11, 2004) "A Pancreatic Islet-Specific MicroRNA Regulates Insulin Secretion," *Nature* 432:226-230.

Rao et al. (Jun. 6, 2006) "Myogenic Factors that Regulate Expression of Muscle-Specific MicroRNAs," *Proc. Nat. Acad. Sci. USA* 103(23):8721-8726.

Sano et al. (Web Release Sep. 30, 2002) "Activation and Function of Cyclin T-Cdk9 (Positive Transcription Elongation Factor-b) in Cardiac Muscle-Cell Hypertrophy," *Nat. Med.* 8(11):1310-1317.

Wu et al. (2003) "NELF and DSIF Cause Promoter Proximal Pausing on the hsp70 Promoter in Drosophila," *Genes Dev.* 17:1402-1414.

Xu et al. (Dec. 2004) "MicroRNAs and the Regulation of Cell Death," *Trends Genet.* 20(12):617-624.

Xu et al. (Apr. 29, 2003) "The *Drosophila* MicroRNA Mir-14 Suppresses Cell Death and is Required for Normal Fat Metabolism," *Curr. Biol.* 13:790-795.

Zhao et al. (Jul. 14, 2005) "Serum Response Factor Regulates a Muscle-Specific MicroRNA that Targets Hand2 During Cardiogenesis," *Nature* 436:214-220.

\* cited by examiner

NELF-A 3'UTR

| | | | |
|---|---|---|---|
| Seed 1 | 1999 | AGTCTAGGGTGT GAG GGGGGC TATGACCAGCCTTGAT | 2032 |
| S1Mut | | AGTCTAGGGTGT GAG▬▬▬▬TATGACCAGCCTTGAT | SEQ ID NO:21 |
| Seed 2 | 1973 | CCTCATGAGGTTGAG GGGACCAAAGGTGACAGCTGGA | 1993 |
| S2Mut | | CCTCATGAGGTTGAG▬▬▬▬AAAGGTGACAGCTGGA | SEQ ID NO:22 |

Fig. 12

USES AND COMPOSITIONS COMPRISING MIRNAS

CROSS-REFERENCE TO RELATED APPLICATIONS

This application is the U.S. national stage application under 35 U.S.C. §371 of International Application No. PCT/EP2007/007131, filed Aug. 3, 2007, which claims benefit of Great Britain Patent Application No. GB 0615609.5 filed Aug. 4, 2006, each of which is hereby incorporated by reference in its entirety.

The present invention relates to the use of miRNAs in therapy, and to compositions comprising them.

MiRs, first transcribed as long primary transcripts (pri-miRs), are processed in the nucleus by the RNase III enzyme Drosha to generate a 60-120 nucleotide precursor containing a stem-loop structure, known as pre-miR. This precursor, exported into the cytoplasm by the nuclear export factor Exportin-5 and the Ran-GTP cofactor, is finally cleaved by the RNase enzyme Dicer to release the mature miR.

Growing evidence indicates that microRNAs (miRs) are implicated in basic cell functions and oncogenesis. MicroRNAs (miR) are small conserved RNA molecules of ~22 nt[1], which negatively modulate gene expression in animals and plants, mostly via base paring to the 3'UTR of target mRNAs leading to mRNA cleavage and/or translation repression[1]. Currently, more than 300 miRs have been identified in humans and other eukaryotic species (miR registry, www.sanger.ac.uk/Software/Rfam/mirna/index.shtml).

MiRs are phylogenetically conserved[2-5] and are involved in a variety of basic biological processes, e.g., cell proliferation and apoptosis[6,7], neural development[2], haematopoiesis[8,9], fat metabolism[10], insulin secretion[11], and stress response[12]. In fact, bioinformatic analysis predicts that each miR may regulate hundreds of targets, thus suggesting that miRs may play a role in almost every biological pathway[13]. Recent studies indicate that miRs are implicated in cancer, where they can act as tumour suppressors or oncogenes[14]. Conversely, their possible involvement in other abnormal conditions, e.g., heart disease, has not been explored yet.

Several miR genes are expressed in a tissue-specific manner[1]. The muscle-specific miR-1 inhibits cardiac myocytic cell (CMC) proliferation via Hand2, a transcription factor regulating ventricular CMC proliferation[15]. On the other hand, miR-1 favours CMC differentiation via a complex circuit. Specifically, miR-1 (a) is activated by muscle differentiation factors such as SRF and MyoD and (b) represses the translation of HDAC4, an inhibitor of muscle differentiation, mainly through the transcription factor MEF2C[15]. In *Drosophila*, dmiR-1 is involved in regulating muscle precursor differentiation[16]. Targets of dmiR-1 comprise Delta, a membrane bound ligand of Notch playing a role in cardiac cell determination[16].

CMCs respond to stress by undergoing hypertrophy, which is mediated by extracellular stimuli, including cytokines or pressure stimuli that activate diverse signal transduction pathways. These, in turn, induce a reprogramming of cardiac gene expression and the activation of "foetal" cardiac genes, e.g., atrial natriuretic factor (ANF), skeletal muscle actin (SkA), and β-myosin heavy chain (β-MHC), encoding proteins involved in contraction, calcium handling, and metabolism. This transcriptional reprogramming correlates with loss of cardiac function[17]. Conversely, improvement in cardiac function in response to drug therapy or implantation of a left ventricular assisting device is accompanied by normalisation of cardiac gene expression[17].

The cardiac-specific miR, miR-133 and miR-1, are critical in determining hypertrophy of cardiac myocyte cells (CMC), and that restoration of levels of expression thereof can alleviate the symptoms of CMC hypertrophy.

Thus, in a first aspect, the present invention provides the use of RNA comprising all, or a substantial part, of SEQ. ID NO. 1 (miR-133) or SEQ. ID NO. 2 (miR-1), preferably SEQ. ID NO. 1, or a mutant or variant thereof, in the manufacture of a medicament for the treatment or prophylaxis of cardiac disease.

SEQ. ID NO. 1 is 3'-<u>UG</u>UCGACCAACUUCCCCUGGUU-5'.

SEQ. ID NO. 2 is 3'-AUGUAUGAAGAAAUGUAAGGU-5'.

It will be appreciated that reference to miR133 includes the minor variants miR133a and miR133b. The sequence of miR133a is that given in SEQ ID NO. 1 above, whist the sequence of miR133b differs in that the 3'-UG of miR-133a (as underlined above) is replaced simply by 3'-A in miR133b. Thus, the sequence of miR133b is 3'-AUCGACCAACUUCCCCUGGUU-5' (SEQ ID NO. 15). Antogmirs of miR133b are also envisaged. Whilst miR133b is preferred, miR133a is even more preferred.

MiRs do not need to correspond directly to that part of the mRNA that they interact with. Accordingly, it is not always clear where the binding site on the mRNA is and, indeed, it is possible that the miR interacts with one or more sites on the same mRNA. In general, however, miRs have been found to bind with the UTR and, although binding of the miRs of the present invention is generally discussed in relation to UTRs, it will be appreciated that any reference to UTR in the context of miR binding also includes reference to any mRNA site to which the miR binds, or with which it interacts.

Preferred antagomirs are the complementary to miR 133 or miR 1, preferably the sequences to SEQ ID NO. 1 and SEQ ID NO. 2 and are provided as:

(5'-ACAGCUGGUUGAAGGGGACAA-3');   SEQ ID NO. 13
and (5'-UACAUACUUCUUUACAUUCCA-3').    SEQ ID NO. 14

In the above SEQ. ID's, the bold septamers are preferred to be conserved, as it is considered that these are seed sequences for initiating binding to the target RNA, so that it is strongly preferred to retain these sequences in any mutants or variants in order to ensure activity.

Figure 7:
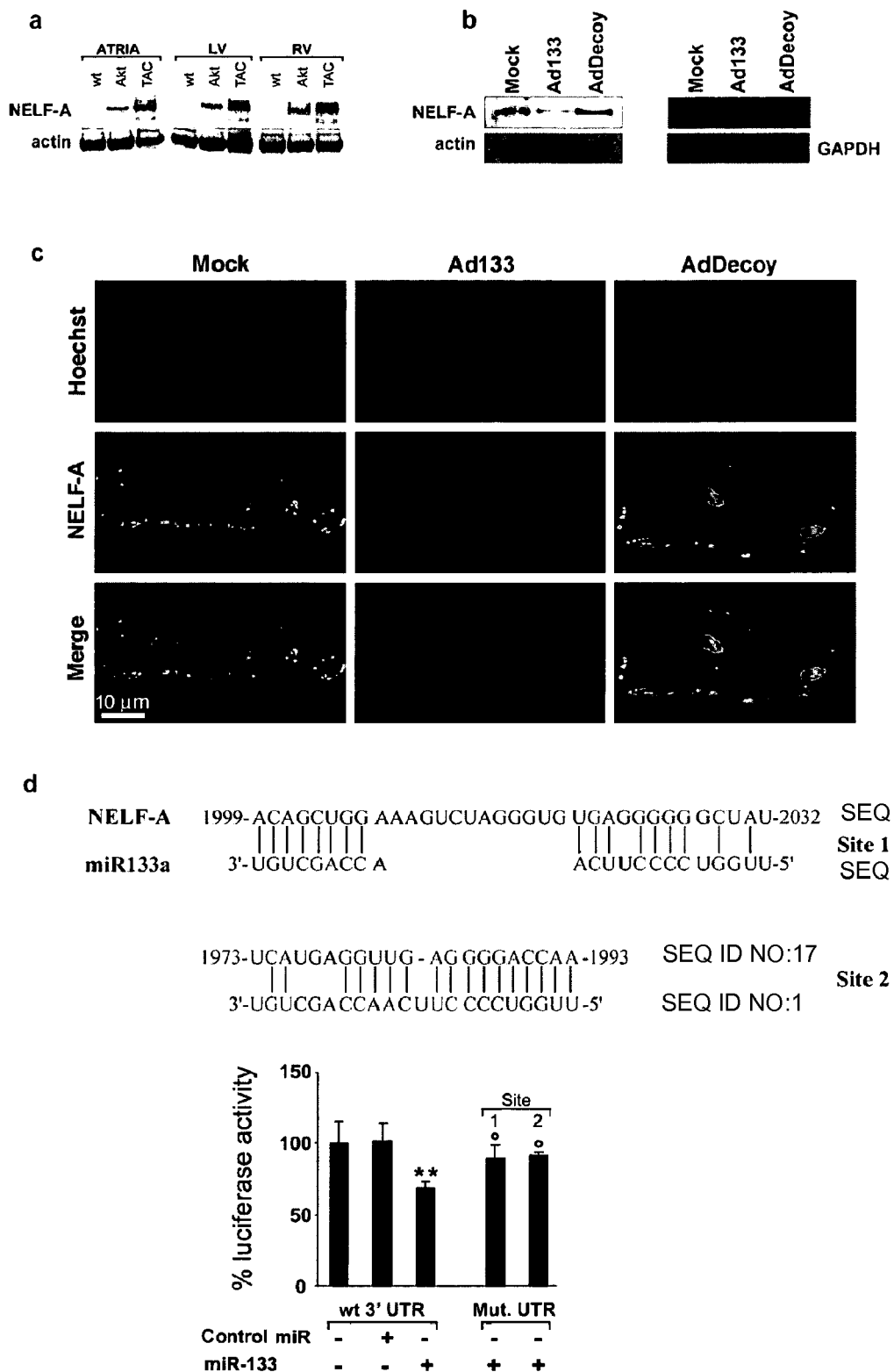
Figure 8:
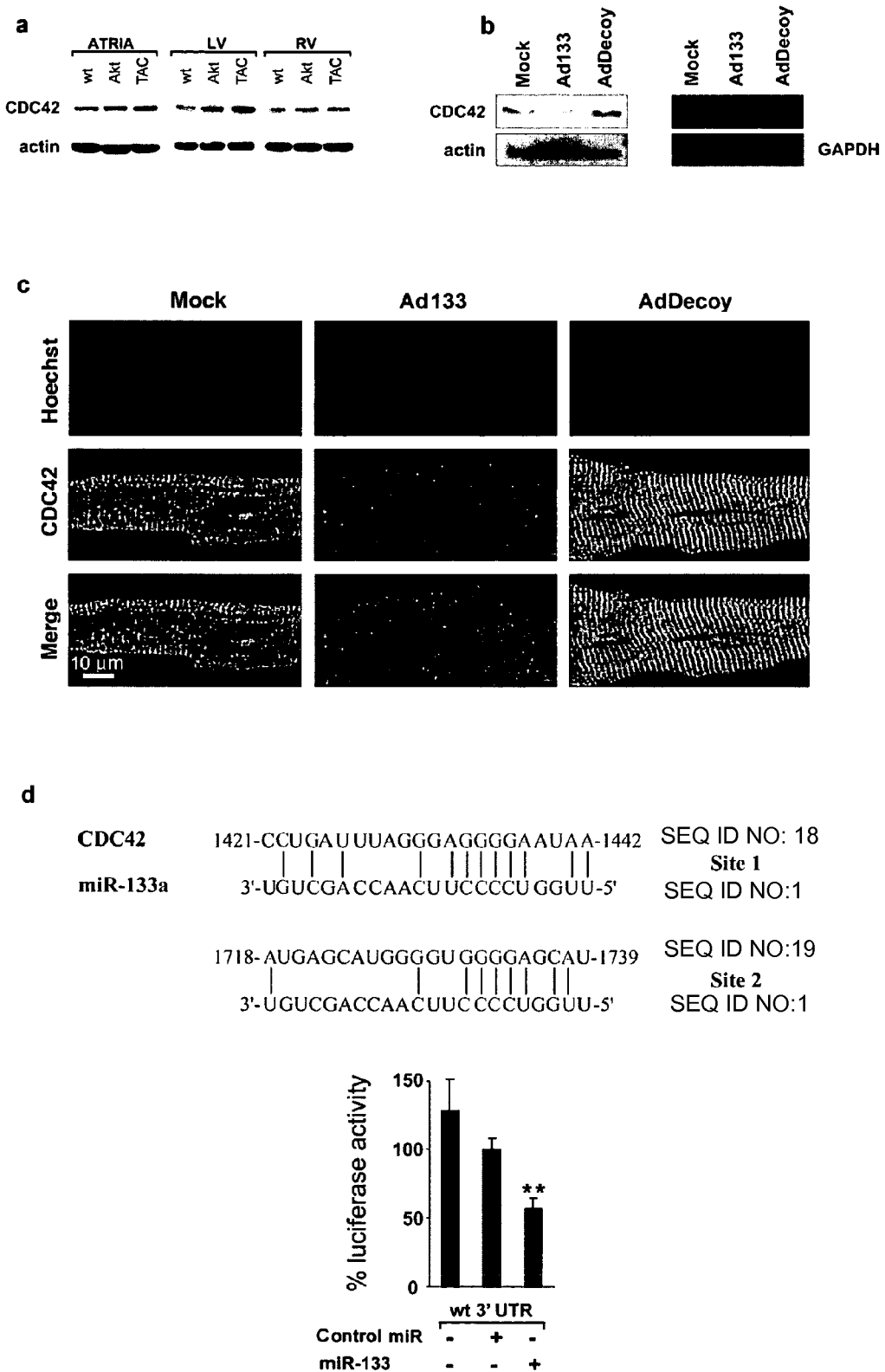

As can be seen from accompanying FIGS. 7 and 8, miR-133 binds to NELF-A and CDC-42 mRNAs, each at 2 putative sites. In none of the 4 sites shown is the match perfect. Thus, it will be appreciated that the sequence of miR-133 may be modified, whilst still binding to the target mRNAs.

The sequence of miR-133 may be mutated or varied by up to 50% whilst still exhibiting sufficient levels of binding to CDC-42 mRNA, but it is generally preferred that mutants and variants differ from miR-133 by no more than 40%, preferably no more than 30% and more preferably no more than 20%. In particular, it is preferred that the sequence difference is 10% or less, and it is most preferred that there be no variation in sequence. However, it may be desirable to truncate SEQ. ID NO. 1 (miR-133) or SEQ. ID NO. 2 (miR-1). This may be by removing one or two nucleotides from each or either end of miR-133. More nucleotides may be removed, if desired, but it is generally preferred to limit the removal of nucleotides to no more than 5 residues, in total.

The RNA of the present invention may consist of the sequence of SEQ. ID NO. 1 or SEQ. ID NO. 2, optionally modified as discussed above. The RNA of the invention may also comprise such a sequence as a part thereof, together with one or more additional sequences to form a longer polynucleotide sequence. It will also be noted that mutants, as discussed below, may comprise additional nucleotides within the sequence, although this is not generally preferred and, where such additions occur, then it is preferred to limit such internal additions to no more than 3 nucleotides, preferably as a spot mutation. Longer polynucleotide sequences arising through additional sequences at one or other, or both, of the 3' and 5' ends should preferably be no longer than the mRNA to which they are binding and, in any case, must be capable of exerting anti-hypertrophic effects in CMCs. Such effects may be measured by inducing hypertrophy and assaying whether the putative RNA is able to counteract the induced hypertrophy, as described in the accompanying Examples.

RNA of the present invention may consist of anywhere up to about 150 nucleotides. This will generally take the form of a primary transcript, which will be cleaved in the cytoplasm to an oligonucleotide of about, or preferably exactly, the length of SEQ. ID NO. 1.

The RNA of the present invention must be capable of exerting anti-hypertrophic effects in CMCs, but such effects need not be exhibited directly by the RNA where intracellular processing of the RNA takes place prior to activity being exhibited.

The preferred RNAs of the present invention comprise at least the cytidine tetramer of SEQ. ID NO. 1 or SEQ. ID NO. 2, and are capable of binding to both CDC-42 mRNA and NELF-A mRNA.

RNA of the present invention has its effect in the CMCs, in general, and any suitable means for introducing the RNA of the invention into the cells is acceptable. Suitable methods include the gene gun and viral capsids. In particular, it is preferred that any delivery method be targeted at CMCs, for example with the vehicle being bound to an antibody recognising a CMC antigen. The invention, therefore, further provides a use as defined, wherein the medicament comprises a vector suitable to introduce the RNA into CMCs.

Treatment with a medicament comprising the RNA of the invention provides short term relief from a hypertrophic condition. If longer term relief is required, then introduction of DNA encoding the RNA of the present invention to the cells is provided as an aspect of the invention. Any suitable techniques for transforming target cells in vivo may be employed, including the use of suitable retroviruses and lentiviruses, for example adenovirus. The DNA encoding the RNA is preferably in the form of an expressible gene, which may express the miR directly, or which preferably expresses a primary transcript, as discussed above. It will be appreciated that any such gene preferably comprises transcription control sequences, particularly for initiation and termination of transcription. Such a gene is particularly present in a plasmid which may simply be used to transfect the target cell, or the delivery vehicle, such as a retrovirus, may suitably be selected to incorporate the DNA into the genome via reverse transcription of an RNA corresponding to the DNA of the invention.

In instances where it is determined that expression of miR-133 is deleterious, then it may be desirable to administer small interfering RNA (siRNA) having an antisense sequence to the RNA of the present invention. Such siRNA does not necessarily have to bind the entire length of the miR, and the skilled person will recognise that all that is required is that the siRNA bind to the miR in such a manner that double stranded RNA (dsRNA) is formed. Formation of dsRNA inhibits the action of the miR and generally leads to digestion of the dsRNA. Suitable means for administering the siRNA are as described above for miR, and it will be appreciated that it is generally not preferred to reduce the level of miR to such an extent that hypertrophy of CMCs occurs.

siRNA of the present invention may also be employed to detect the presence of miR-133. For example, labelled siRNA may be used to form a plate to detect the presence of the desired miR. Anti-miR-133 antibodies may also be employed in a similar fashion to determine levels of miR in a sample, and determination of the levels of miR-133 may be used to indicate the presence or absence, or tendency towards, CMC hypertrophy.

The endogenous expression of miR-133 is dramatically decreased in cardiac hypertrophy in both in in vitro and in in vivo models. MiR-133 enforced expression suppresses hypertrophy hallmark parameters, including increased CMC size, protein synthesis, cytoskeletal structural reorganization and re-expression of foetal genes. Conversely, suppression of miR-133 by decoy sequences induces a dramatic CMC hypertrophy, which is even more pronounced than after agonist treatment. We have also established that the targets of miR-133 include the nuclear factor NELF-A, involved in heart genesis, and the signal transduction kinase CDC42, implicated in hypertrophy. Accordingly, miR-133 over-expression or down-modulation causes an inverse fluctuation of NELF-A and CDC42 at protein level, whereas mRNA expression is unmodified. Without being bound by theory, it appears that miR-133 is a master gene controlling cardiac hypertrophy.

As noted above, miR need not be 100% faithful to the target, sense sequence. Indeed, complete matching can lead to cleavage of the target mRNA through the formation of dsRNA. While the formation of dsRNA and cleavage of target mRNA is included within the scope of the present invention, it is not a requirement that the RNA be 100% faithful to the UTR, provided that the RNA is capable of binding the target 3' UTR to inhibit or prevent translation.

The present invention further provides mutants and variants of these miRs. In this respect, a mutant may comprise at least one of a deletion, insertion, inversion or substitution, always provided that the resulting miR is capable of interacting with the 3' UTR to inhibit or prevent translation of the associated coding sequence. Enhanced homology with the 3' UTR is preferred. A variant will generally be a naturally occurring mutant, and will normally comprise one or more substitutions.

The RNAs of the present invention may be provided in any suitable form to the target site. In this respect, the target site may be in vivo, ex vivo, or in vitro, for example, and the only requirement of the RNA is that it interacts with the target 3' UTR sufficiently to be able to inhibit or prevent translation of the ORF.

The RNA may be provided directly, or a target cell may be transformed with a vector encoding the RNA directly, or a precursor therefor. Suitable precursors will be those that are processed to provide a mature miR, although it is not necessary that such precursors be transcribed as long primary transcripts, for example.

Where the RNA is provided directly, then this may be provided in a stabilised form such as is available from Dharmacon (www.dharmacon.com, Boulder, Colo., USA).

More particularly, the present invention provides the use of miR-133 in therapy.

Levels of RNA to be administered will be readily determined by the skilled physician, but may vary from about 1 mg/kg up to several hundred micrograms per kilogram.

Preferred methods of delivery of the antisense miRNA or sense inhibitors may be by any gene therapy method known in the art, as will be readily apparent to the skilled person. Such methods include the so-called "gene-gun" method or delivery within viral capsids, particularly adenoviral or lentiviral capsids encapsulating or enclosing said polynucleotides, preferably under the control of a suitable promoter.

Preferred means of administration by injection include intravenous, intramuscular, for instance. However, it will also be appreciated that the polynucleotides of the present invention can be administered by other methods such as transdermally or per orally, provided that they are suitably formulated.

The present invention also encompasses a polynucleotide sequence, particularly a DNA sequence, which encodes the microRNAs of the present invention, operably linked to a suitable first promoter so that the MicroRNAs can be transcribed in vivo. Similarly, the present invention also provides a polynucleotide, particularly DNA, providing polynucleotides encoding the sense microRNA inhibitors of the present invention, also operably linked to a suitable second promoter for in vivo expression of said sense microRNA inhibitors.

Thus, (a) miR-133 and miR-1 expression is inversely related to cardiac hypertrophy in vivo. Further, (b) functional studies indicate that overexpression of miR-133 in CMCs inhibits the increase of both CMC size and the other "hallmark" parameters defining hypertrophy, while, conversely, (c) blocking of endogenous miR-133 or miR-1 through a decoy sequence induces, per se, a dramatic CMC hypertrophy, even in the absence of any hypertrophic stimulus. Significantly, these functional studies were performed on both neonatal and adult CMCs, in vitro as well as in vivo.

We have identified two targets of miR-133, CDC42 and NELF-A, which may underlie the establishment of hypertrophy. The mechanism of action of CDC42 is already delineated, whereas the functional pathway of NELF-A remains elusive. CDC42 is associated with the cytoskeletal restructuring taking place during hypertrophy[28,29], while NELF-A regulates the activity of RNA pol II[26]. In this regard, NELF-A interacts with the cdk-9/cyclin T complex[30], which regulates RNA synthesis during hypertrophy by interacting with RNA polymerase II[31]. It is possible that, the involvement of NELF-A in cardiac hypertrophy and development is RNA pol II-dependent.

Although only two targets have yet been identified, it is possible that further targets will be identified. The in vitro studies indicate that total suppression of miR-133 by AdDecoy causes per se a striking hypertrophy, which is even more pronounced than following induction by standard agonist stimuli. Specifically, the AdDecoy causes an increased expression of each of the hallmark molecules upmodulated during hypertrophy. This strongly suggests that miR-133 functions as a "master gene" controlling multiple primary targets, thereby shifting heart gene expression from the physiological to the hypertrophy specific program.

It is likely, therefore, that (a) differential analysis of protein expression in normal versus miR-133 suppressed CMCs may lead to discovery of new molecules underlying heart hypertrophy. Accordingly, the present invention further provides a method for investigating CMC hypertrophy, comprising modulating levels of miR-133 in a culture of CMC cells or cells providing a model therefore. In addition, (b) miR-133 levels are modified in a "disease" in vivo model, e.g., pressure overload-induced hypertrophy, while in vivo functional studies indicate that miR-133 overexpression or suppression either inhibits or induces cardiac hypertrophy respectively.

Thus, the present invention envisages the use of miR-133 in the diagnosis and therapy of myocardial diseases, particularly heart hypertrophy and failure.

There is a potential interaction of the bicistronic miR-133 and miR-1 in cardiac hypertrophy. In skeletal myoblast culture miR-133a and miR-1, while transcribed in the same primary RNA, promote either differentiation or proliferation respectively[32]. In vivo models indicate that in heart hypertrophy miR-133 and miR-1 are downmodulated according to an identical pattern (FIG. 1) suggesting that these two miRs may functionally interact to unblock the translation of two coordinate sets of target mRNAs underlying hypertrophy development.

The present invention will now be described with reference to the accompanying Figures and Examples, which are not limiting on the present invention. All references cited herein are incorporated by reference, unless otherwise apparent.

EXAMPLES

Materials and Methods

Human Tissues and Mice

Human embryos and foetuses were obtained by legal abortions at 5-10 weeks after fertilisation, according to institutional guidelines[33]. A fully informed consent was obtained in advance from the mothers. The age was carefully established by morphologic staging according to standard multiple criteria. Different organs were dissected under an inverted microscope and stored under liquid nitrogen until total RNA extraction. Experiments on C57/B16 mice were performed according to institutional guidelines.

MiR Analysis

Microarray

Microarray analysis was performed as described[18]. Processed slides were scanned by ScanArray XL5K and the expression level analysed by QUANTARRAY software (PerkinElmer). Raw data were analysed using GENESPRING, software version 6.1.1 (Silicon Genetics): the average value of each miR was transformed to convert negative values to 0.01 and normalised on its median using a per-chip $50^{th}$ percentile method[8,18].

Northern Blot

Total RNA, enriched for low molecular weights, was isolated according to the acid phenol/guanidinium thiocyanate/chloroform standard procedures and hybridised as described[6]. The probes used are:

```
miR-133a,
                                        (SEQ. ID NO. 3)
5'-ACAGCTGGTTGAAGGGGACCAA-3', miR-1,
                                        (SEQ. ID NO. 4)
5'-TACATACTTTACATTCCA-3'
and Met-tRNA,
                                        (SEQ. ID NO. 5)
5'TGGTAGCAGAGGATGGTTTCGATCCATCGACCTCTG-3',
``` as a loading control.

The expression levels were analysed by the Scion Image Software (www.scioncorp.com).

In Situ Hybridisation

Seven-μm OCT sections from 10-18-day murine embryos, 1-day-old and adult mice were paraffin fixed, treated with 10 mg/ml proteinase K and hybridised with $^{33}$P miR-133 probe/ ml. The antisense RNA oligo was 5' end-labelled and hybridisation was carried out overnight at RT according to standard procedures. Counterstaining was performed in 0.02% toluidine blue, and slides were mounted in Permount solution. Images were taken using an Olympus microscope.

In Vivo Experiments

Induction of Pressure Overload Cardiac Hypertrophy.

C57BL/6 mice (Harlan) were used. The pressure-overload model was obtained through transverse aortic banding (TAC) under anaesthesia with ketamine-xylazine (100 or 2.5 mg/Kg respectively) mixture, as described[34].

Akt Transgenic Mice

Transgenic mice with cardiac specific overexpression of constitutively active Akt were previously described[19]. Specifically, Akt overexpression induces a significant increase in CMC size and concentric LV hypertrophy.

Echocardiographic Analysis.

Transthoracic echocardiography, under isoflurane anesthesia, was performed before and one week after TAC with the use of an HP Sonos 5500 echocardiograph. Two-dimensional, M-mode, and Doppler echocardiographic examination were performed using a 15 MHz linear transducer, as described[35].

Plasmids and Vectors

Adenoviral miR-133a (Ad133). Mir-133a precursor DNA was PCR-amplified from mouse genomic DNA by using AccuPrime Taq DNA polymerase high fidelity (Invitrogen). The amplified fragment (683 bp) was first subloned in pcDNA3 (Invitrogen), then inserted under CMV promoter into an adenoviral vector, VQ Ad5CMV K-NpA (ViraQuest Inc.) for virus production.

Figure 10:
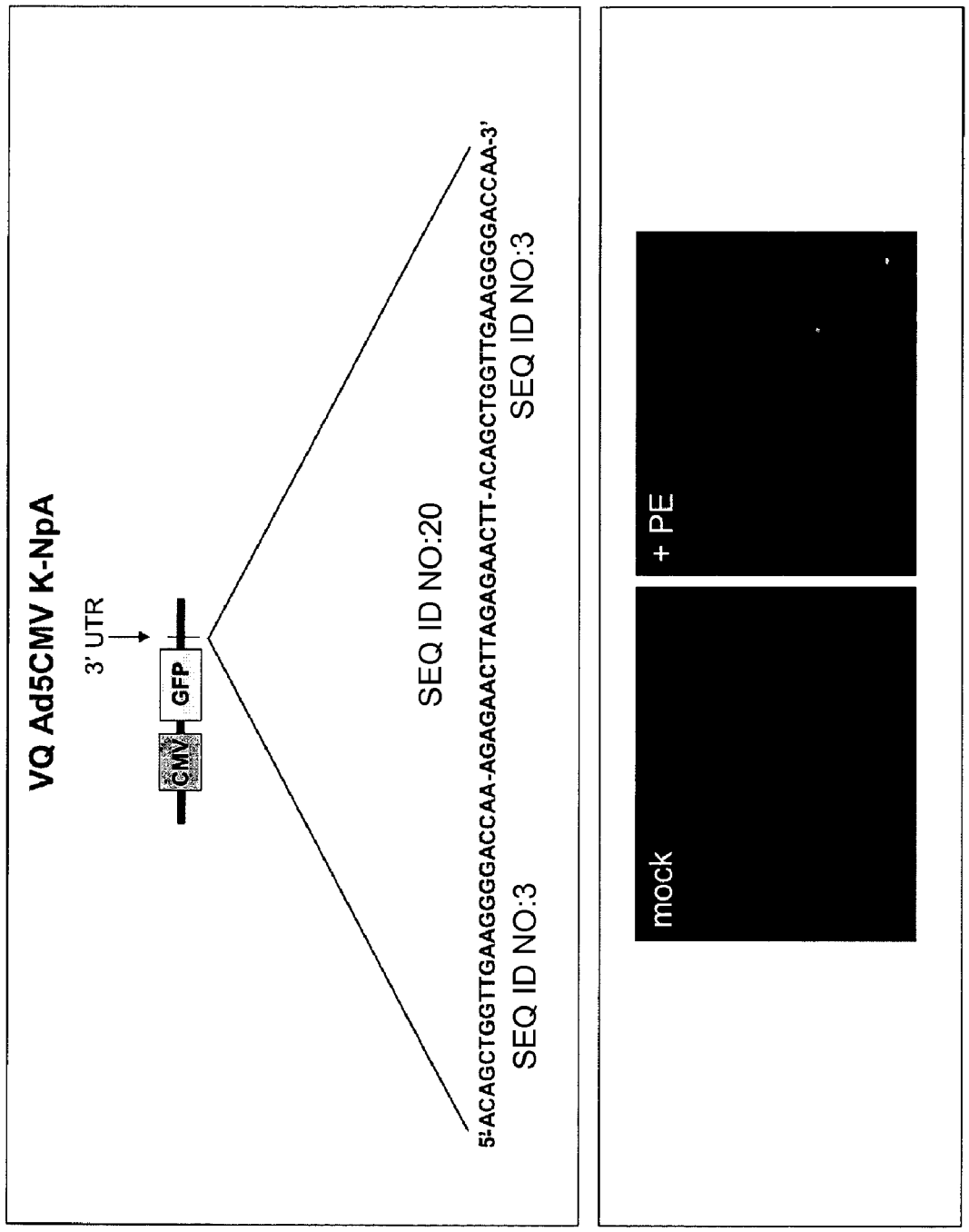

Adenoviral miR-133a Decoy (AdDecoy) (FIG. 10). The EGFP 3'UTR was modified to include tandem sequences complementary to miR133a ("decoy") separated by a space: the EGFP-modified 3'UTR was then subcloned into VQ Ad5CMV K-NpA vector driven by CMV (top panel). When miR levels are downregulated, the EGFP sensor levels increase (bottom). More important, the decoy sequences sequester the endogenous miR-133, blocking its activity (FIG. 3b, right panel).

pGL-3'UTR plasmid. For luciferase reporter experiments, the 3'UTR segments of NELF-A and CDC-42, predicted to interact specifically with miR-133, were amplified by PCR (AccuPrime) Taq DNA polymerase high fidelity (Invitrogen) from murine genomic DNA. The 3' UTR from target genes were subcloned by standard procedures into pGL3-Promoter vector (Promega) using Xba I site, immediately downstream from the stop codon of luciferase gene. For NELF-A, a 3'UTR of 250 by fragment was amplified. For CDC-42 3'UTR, a 1400 by fragment was amplified.

In vitro Functional Studies

Isolation, Culture and Treatment of Mouse Cardiomyocyte Cells (CMCs)

Neonatal CMCs were isolated from 1-day-old pups following standard enzymatic technique[36]. CMCs were cultured for 24 h in D-MEM (Sigma) supplemented with penicillin (100 U ml$^{-1}$), streptomycin (100 μg ml$^{-1}$), HEPES (25 mM), glutamine (2 mM), 10% newborn calf serum and 5% foetal bovine serum (FBS). Culture medium was switched to serum-free medium 24 h before treatment. Agonist treatment involved addition of 100 μM phenylephrine (PE) or 100 nM endothelin-1 (ET1); cells were analysed 48 h after treatment. Adenoviral infection (m.o.i. specified in Results) was performed in serum-free medium; 5 h after infection the medium was replaced and the cells were further incubated for 48 h. When used in combination with Adenoviral vectors, 100 μM PE or 100 nM ET1 were added when fresh medium was replaced after infection. Adult CMCs were isolated from 12-16-weeks-old male mice using standard enzymatic technique[36]. Freshly isolated CMCs were plated at a density of 0.5 to $1\times10^4/cm^2$ in dishes precoated with 20 μg/mL laminin (Collaborative Biomedical Products) in D-MEM supplemented with 1 mM $CaCl_2$, 15 mM Butanedione monoxime, 25 mM HEPES and penicillin plus streptomycin 1%. Cells were then treated as described[36].

Fluorescence Microscopy

Cultured CMCs were fixed in 4% PFA, rinsed in PBS, permeabilised with blocking buffer for 20 min (0.1% triton X-100, 1% normal donkey serum, 1% cold-water fish gelatin and 20 mM glycine), and finally stained overnight at 4° C. with anti-ANF (R&D Systems), anti-NELF-A/WHSC2 (Novus Biologicals) or anti-CDC42 (Cell Signalling) Abs in diluted buffer. After an extended wash, secondary antibodies (Sigma) and/or Alexa Fluor 546 phalloidin (Molecular Probes) were added for 1 h at 4° C. Afterwards, the cells were again washed extensively with buffer. The slides were stored in a refrigerator until imaged by Bio-Rad Radiance 2000 Confocal/2-Photon Microscope. Experiments were repeated at least twice to confirm the fluorescence patterns.

Western Blot

The expression of NELF-A and CDC42 was evaluated in total lysates by Western blot according to standard procedures. Anti-NELF-A (Abcam) and anti-CDC42 (Cell Signaling) polyclonal antibodies were diluted 1:2000 in TBST-1% milk and 1:1000 in TBST-5% BSA, respectively. As internal controls anti-actin (Oncogene Research Products) monoclonal antibody was used.

[$^3$H]Leucine Uptake Assay.

One-day-old neonatal mouse CMCs were used to assess protein synthesis by incorporation of [$^3$H]leucine. After 24 h serum starvation, CMCs were mock, Ad133 or AdDecoy superinfected and/or treated with the drugs for 48 h prior to 1 μCi/ml [$^3$H]leucine addition. Cells were further incubated for 12 h before radioactivity assay.

Measurement of Cell Size

Surface areas, perimeter, length and width of CMCs were measured using NIH Image J 1.32j software (http://rsb.info.nih.gov/ij/). An average of 350-400 CMCs cells were chosen at random for measurement of cell sizes.

Dot Blot

Total RNA from control and treated neonatal or adult CMCs was isolated using Trizol Reagent (GIBCO BRL). For dot blotting 2 μg of denatured RNA were applied to nylon membranes (BrightStar-Plus, Ambion) under vacuum using a microfiltration apparatus (BioRad). Prehybridisation (1 hr, 55° C.) and hybridisation (overnight, 55° C.) were performed in UltraHyb buffer (Ambion) supplemented with 10 mg/ml salmon sperm DNA. [$^{32}$P]dATP-labeled cDNA probes were obtained by end-labeling of the following oligonucleotides:

ANF (SEQ. ID NO. 6)
(5'AATGTGACCAAGCTGCGTGACACACCACAAGGGCTTAGGATCTTTTG

CGATCTGCTCAAG);

Cardiac actin (SEQ. ID NO. 7)
(5'TGTACAATGACTGATGAGAGATGGGGAGGGGGCTCAGAGGATTCCAA

GAAGCACAATAC);

Skeletal actinin

-continued (SEQ. ID NO. 8)
(5'TGGAGCAAAACAGAATGGCTGGCTTTAATGCTTCAAGTTTTCCATTT

CCTTTCCACAGGG);

α-MHC
(SEQ. ID NO. 9)
(5'CGAACGTTATGTTTATTGTGTATTGGCCACAGCGAAGGGTCTGCTGA

GAG)

β-MHC
(SEQ. ID NO. 10)
(5'-GCTTTATTCTGCTTCCACCTAAAGGGCTGTTGCAAAGGCTCCAGGT

CTGAGGGCTTC);

GADPH
(SEQ. ID NO. 11)
(5'GGAACATGTAGACCATGTAGTTGAGGTCAATGAAG).

In Vivo Functional Studies

Animals were treated for in vivo gene transfer with either Ad133 or AdDecoy using a method modified from Ikeda et al[37]. Akt Tg or wt mice were used for Ad133 or AdDecoy gene transfer respectively. Mock infection was applied in the controls. Each group included 10 adult mice. Animals were initially anaesthetized with a single dose of ketamine (50 mg/kg BW) xylazine (2.5 mg/Kg BW) and then intubated and ventilated with a pressure-controlled respirator maintained on 0-5-2.0% isofluorane in $O_2$. Via a small left anterior thoracotomy, ligatures were looped around the aorta and pulmonary artery and threaded through occluder tubes. The right carotid artery was cannulated for measurement of arterial pressure and performing injections with the tip of the catheter placed above the aortic valve. The animals were cooled down to a core temperature of 19-21° C. and a heart rate of 80-100/min was reached. The pulmonary artery and aorta were occluded and three injections were made into the proximal aortic root: specifically, (1) CP solution (110 mM NaCl, 10 mM KCl, 1.2 mM $CaCl_2$, 16 mM $MgCl_2$ and 10 mM $NaHCO_3$, supplemented with 2 ng Substance P, total volume 100 μl); (2) 3 s later CP solution containing 25 mM KCl and 2 ng Substance P to achieve the arrest of the heart (100 μl); (3) 45 s later an Ad vector ($9.2 \times 10^{10}$ virus particles) in CP solution with 10 mM KCl and 1 ng Substance P (75 μl). Three minutes later both snares were released and an intraaortic infusion of dobutamine (20 μg/kg/min) started. When the arterial pressure reached about 65-70 mm Hg, the animals were placed on a heating pad (42° C.), the chest was closed and intrathoracic air evacuated. Animals were extubated upon spontaneous breathing and closely observed until fully awake. All protocols were approved by the University of California, San Diego Animal Subjects Committee Target Analysis Luciferase Assay 293FT or HeLa cells ($5 \times 10^4$ cells per well) were transfected with: (a) 0.02-0.8 mg of pGL3-3' UTR plasmid respectively, (b) 20 pmol of either a stability-enhanced 2i-O-Methyl non-targeting RNA control of miR-133a oligonucleotides (Dharmacon Inc.), (c) Lipofectamine 2000 (Invitrogen). In order to evaluate the percentage of transfected cells a GFP-Emd plasmid was also transfected. At 48 h, after FACS analysis, cells were lysed and their luciferase activity measured by using the FemtomasterFB 12 (Zylux). The relative reporter activity was obtained by normalisation to the pGL3-3'UTR control oligonucleotide cotrasfection.

3'UTR NELF-A mutagenesis (FIG. 12). A six nucleotides mutation was inserted in the two "seed" sequences interacting with miR-133. Modified and HPLC purified oligomers (Invitrogen) were used for amplification, performed with Pfu enzyme, and followed by mutagenesis (Invitrogen).

Statistical Analysis

Statistical and frequency distribution analysis was performed by GraphPad Prism 4.0. Differences between two or three groups were compared with Student's t-test or one-way ANOVA respectively. A value of $p < 0.05$ or less was considered to be statistically significant.

Results

MiR-133 and miR-1 are Selectively Expressed in Heart and Skeletal Muscle.

To investigate the possible role of miR genes in CMC hypertrophy we evaluated the expression profile of miRs in embryonic and adult heart from human and mouse under both physiological and pathological conditions. The analysis was performed by using a microarray chip containing gene-specific 40-mer oligonucleotide probes, generated from 161 human and 84 mouse precursors miRs[8,18]. Two miRs, miR-133 and miR-1 were markedly reduced in hypertrophic heart. Microarray chip and Northern blot analysis revealed that both miR-133 and miR-1 are specifically expressed in heart and skeletal muscle from human embryonic and adult tissue (FIG. 9a,b). As shown by microchip analysis miR-133 is also expressed in mouse heart and skeletal muscle tissue and miR-133 expression is increased in developing mouse embryos from day E12 through at least day E17 (FIG. 9d). This was confirmed by in situ hybridisation, which demonstrated that miR-133 is selectively expressed in embryonic heart and skeletal muscle, whereas it is virtually absent from other tissues (FIG. 9d, right).

MiR-133 and miR-1 Levels are Inversely Related to Cardiac Hypertrophy.

To determine whether expression of miR-133 and miR-1 is modulated during cardiac hypertrophy we analyzed two mouse models: (a) transverse aortic arch constricted (TAC) mice and (b) Tg mice with selective cardiac overexpression of the Akt active mutant[19] (see haemodynamic data in Table 1). In the first model, multiple signal transduction pathways are induced simultaneously by pressure overload, leading to CMC hypertrophy[20]. In the second one, hypertrophy is mediated by the downstream effects of Akt on mRNA translation and gene expression[21]. One week after TAC hearts were weighed and separated in left ventricle, right ventricle and atria. Sham operated and non-transgenic littermate controls were included. In TAC-treated mice, myocardial hypertrophy was associated with an increased expression of cardiac foetal genes (ANF, SkA, and β-MHC), as expected (results not shown). As shown by Northern blot analysis cardiac hypertrophy in both TAC-treated and Akt over-expressing hearts resulted in reduced expression levels of both miR-133 and miR-1 (FIG. 1a,b; see also Table 2). The decrease was particularly prominent in the left ventricle (2-fold in both models) and in atria (2-fold in TAC hypertrophy and 3-4-fold in Akt Tg mice). In right ventricle both miR-133 and miR-1 expression were significantly reduced in Akt Tg mice, whereas no decrease was observed in the TAC model, which is not coupled with right ventricular hypertrophy (Table 2). Altogether, the data from these in vivo models indicate an inverse correlation between miR-133 and miR-1 expression and myocardial hypertrophy.

Overexpression of MiR-133 Inhibits Cardiac Hypertrophy In Vitro.

Figure 2:
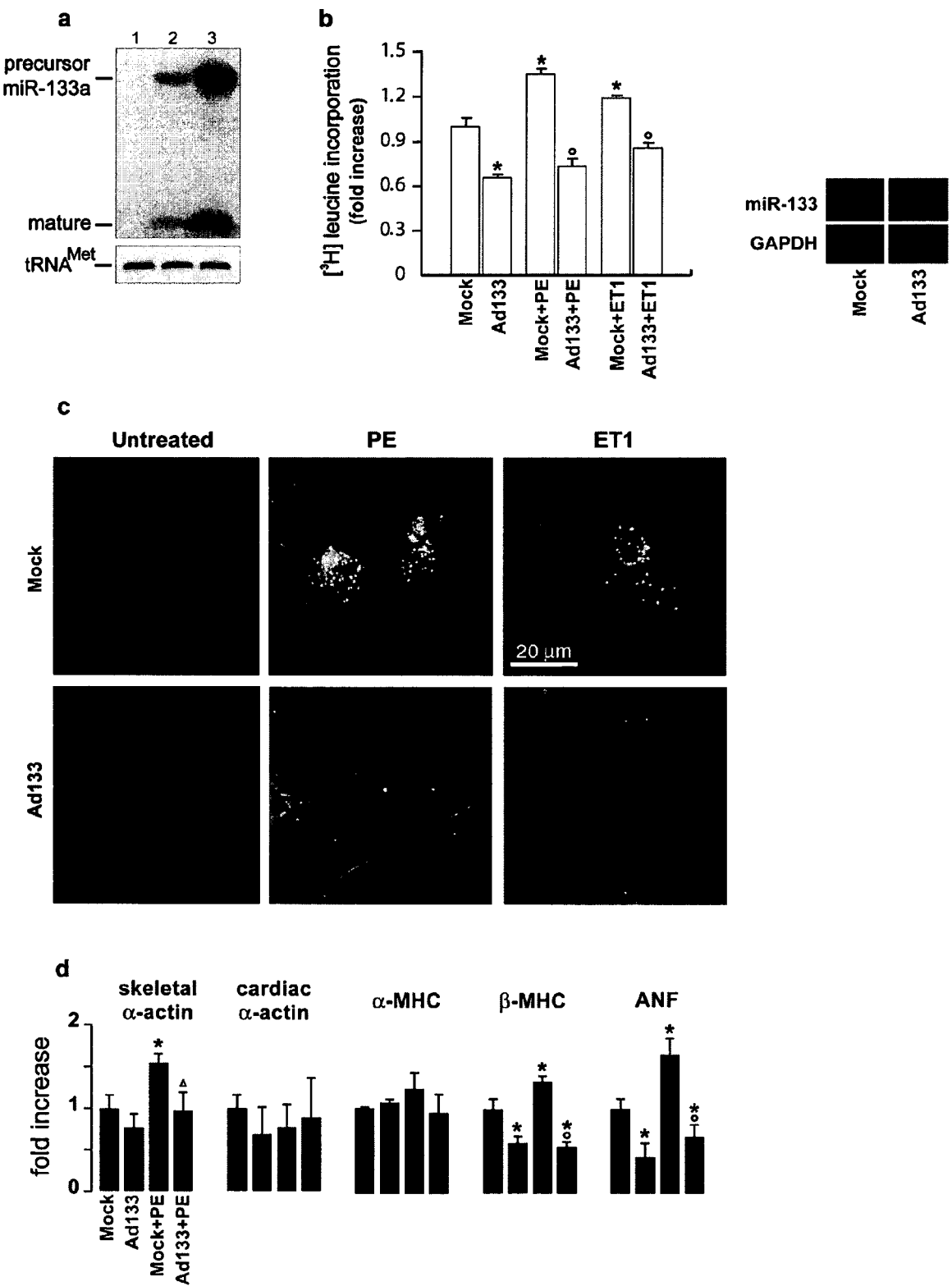

To assess the functional significance of these observations, we tested the effects of miR-133 over-expression in an in vitro model of CMC hypertrophy. Neonatal mouse CMCs were infected with an adenoviral vector containing an expression cassette of 683 by from the murine miR-133a-2 precursor sequence (Ad133), which is processed into the mature miR (FIG. 2a). To induce in vitro CMC hypertrophy as a model of in vivo hypertrophy we used phenylephrin (PE) or endothelin 1 (ET) treatment (FIG. 2)[17]. Distinctive hallmarks of in vitro agonist-induced hypertrophy are: i) increased cell size, ii) enhanced protein synthesis, as measured by $^3$[H]-Leucine incorporation, iii) up-modulation of foetal genes, including ANF, SkA and β-myosin heavy chain, iv) acto-myosin chain rearrangement and subsequent cytoskeletal reorganisation, and v) perinuclear localisation of ANF protein. All these effects, induced by PE and ET, were prevented by CMC infection with Ad133 (FIG. 2), thereby indicating that miR-133 controls the molecular mechanisms underlying CMC hypertrophy.

Suppression of Endogeneous miR-133 by "Decoy" Sequences Induces Cardiac Hypertrophy In Vitro.

Figure 3:
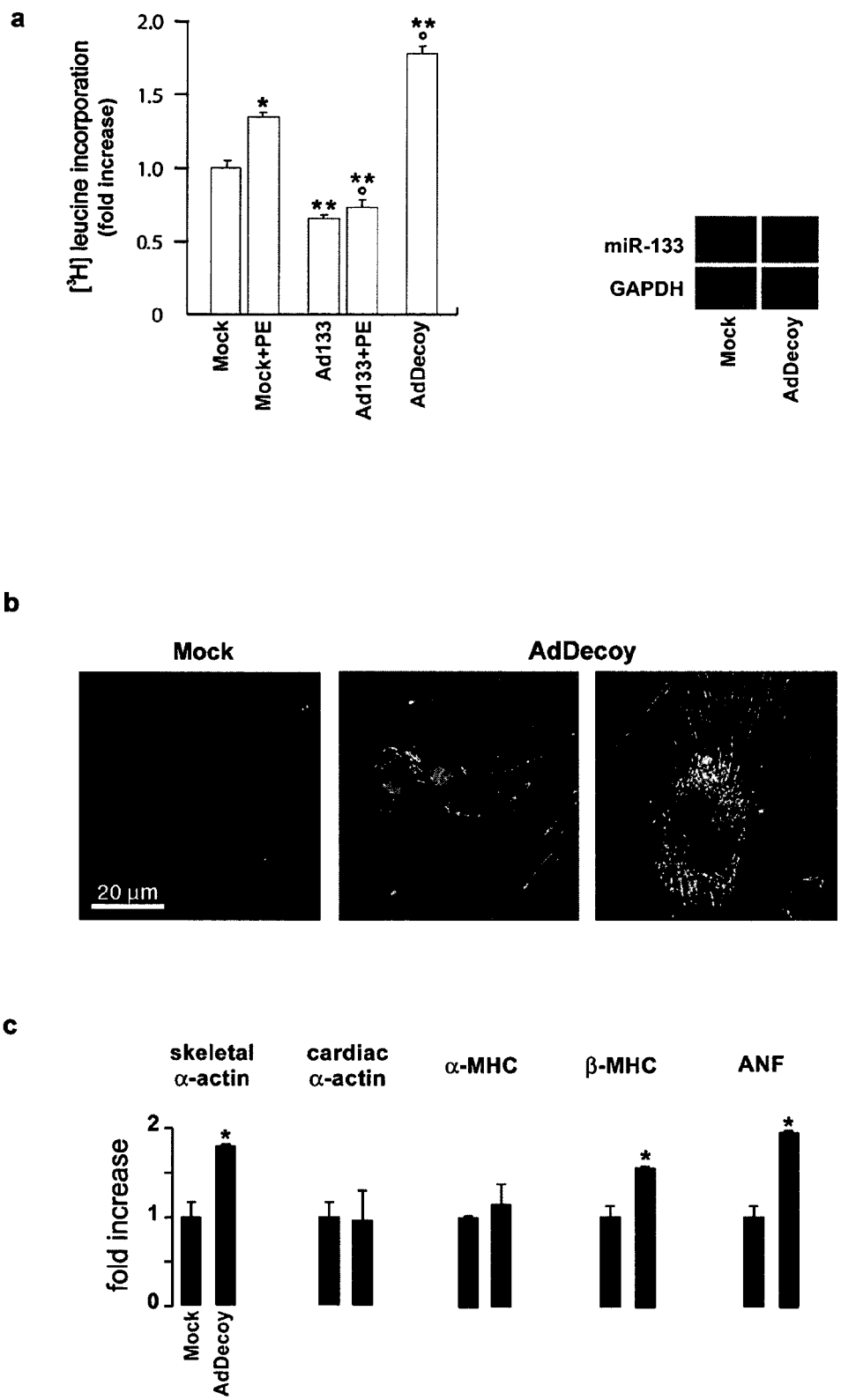

To analyse the functional consequences of the inhibition of endogenous miR-133 expression, we constructed an Ad vector with an expression cassette composed of an EGFP reporter gene linked at the 3' UTR with tandem "decoy" sequences complementary to murine miR-133a (AdDecoy, see FIG. 10, top). A similar approach has been recently reported in hematopoietic cells[22]. AdDecoy infection of neonatal murine CMCs revealed a marked increase in EGFP expression in PE-induced hypertrophy as compared to unstimulated cells. This result indicates that a reduction of miR-133 expression prevents its binding to decoy sequences, thus enabling EGFP mRNA to be translated (FIG. 10, bottom). We then performed in vitro functional assays: AdDecoy infection of neonatal murine CMCs caused a dramatic hypertrophy, based on $^3$[H]-leucine uptake and foetal gene expression, while fully suppressing the level of miR-133 (FIG. 3). Strikingly, the infection induced an increase of $^3$[H]-leucine, which was significantly higher than that induced by PE (FIG. 3a). Moreover, embryonic stress genes and peri-nuclear localisation of ANF, as well as cell size parameters were also markedly increased by AdDecoy (FIG. 3b, c and data not shown).

Figure 11:
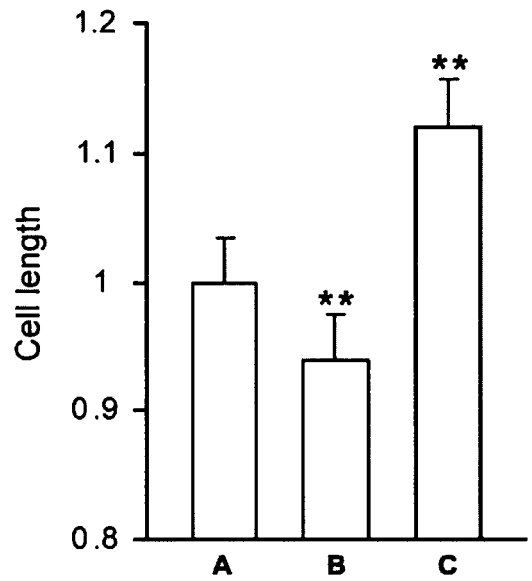
Figure 11:
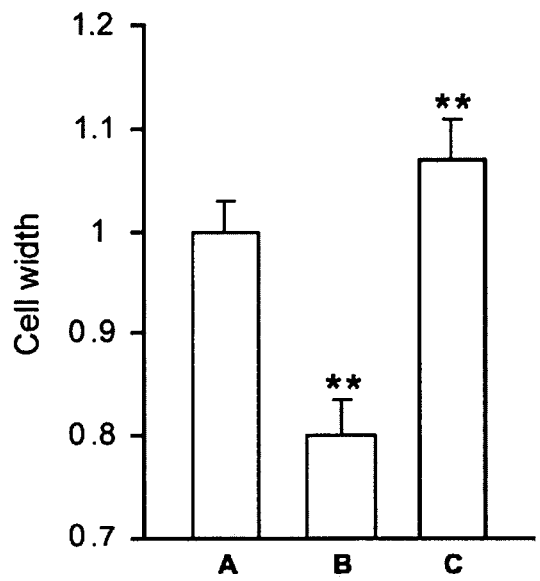
Figure 11:
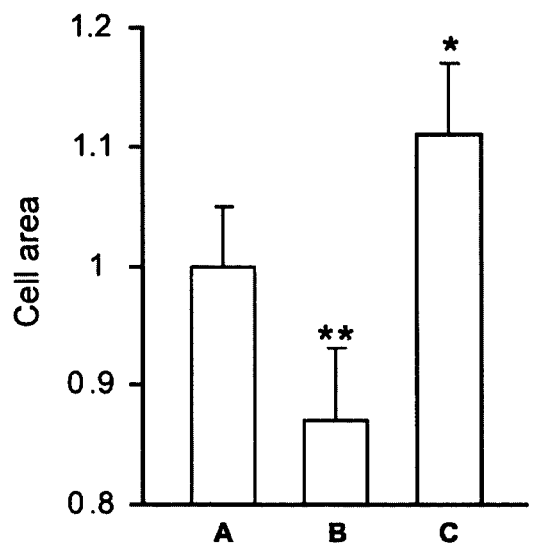
Figure 11:
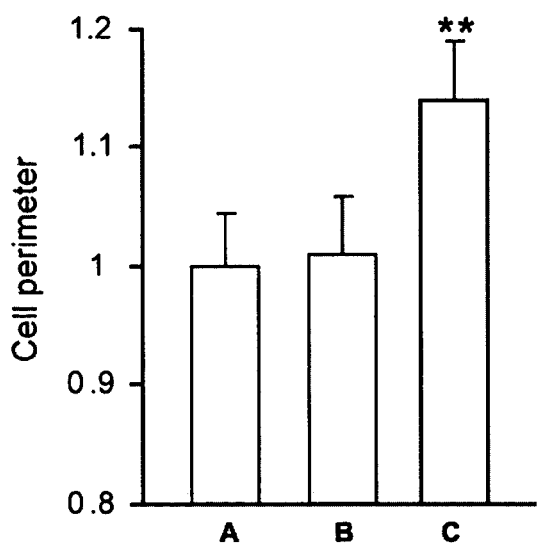

Finally, adult mouse CMCs were infected with AdDecoy or Ad133 to determine whether the above results could be reproduced in a similar, yet distinct model system. In line with neonatal CMC experiments, suppression of endogenous miR-133 with decoy sequences increased adult CMC size, while miR-133 overexpression exerted an opposite effect (FIG. 11).

Altogether, these results indicate that miR-133 plays a pivotal role in heart hypertrophy. Particularly, miR-133 down-modulation and hypertrophy are quantitatively related. In fact, agonist treatment causes a reduced miR expression coupled with hypertrophy, while the AdDecoy induces total miR suppression and a more pronounced hypertrophy.

MiR-133 and miR-1 Modulate Cardiac Hypertrophy In Vivo.

Our in vitro data strongly suggest that miR-133 is a potent modulator of cardiac hypertrophy. To determine the effect of miR-133 on hypertrophy in vivo, we performed a series of experiments based on transcoronary gene delivery to the myocardium of adult mice [23]. Specifically, we delivered AdDecoy to wt mice and Ad133 to Akt Tg animals.

The wt mouse myocardium infected with AdDecoy was evaluated 14 days after gene transfer (FIG. 4a). Analysis of isolated left ventricular CMCs revealed a significant increase in cell size, as compared to mock control values (mean±SD AU values, 0.139±0.003 versus 0.094±0.005 respectively, P<0.001) (top panels). This finding was further supported by the up-regulation of cardiac hypertrophy markers (bottom panel). Notably, only ~40% of left ventricle CMCs were infected (as evaluated in the control group on the basis of GFP expression, data not shown) and miR-133 level was mildly reduced (0.69±0.04 fold, data not shown): in view of these findings, the AdDecoy effects are particularly striking. Interestingly, miR-1 expression was also reduced (0.81±0.07, not presented), suggesting a link between the two miRs.

Since miR-133 over-expression inhibits CMC hypertrophy in vitro, we tested the effect of Ad133 infection on cardiac hypertrophy in Akt Tg mice (FIG. 4b). Fourteen days after Ad133 infection, over-expression of miR-133 resulted in a reduction in left ventricle CMC cell size (0.485±0.019 and 0.333±0.007 AU in mock versus Ad133 injected mice, respectively, P<0.05) (top panels), while inducing a significant decrease in the expression of embryonic genes, except for skeletal α-actin (bottom).

Altogether, the results obtained in these two models complement and strengthen each other to indicate that miR-133 is an important modulator of heart hypertrophy in vivo, in line with our in vitro functional studies.

We then conducted another set of experiments aimed at determining the effect of miR-133 inhibition through overexpression of a decoy sequence in vivo. We generated a construct in which expression of miR-133 or its decoy is driven by the tetracyclin-inducible (Tet) operon. A DNA fragment containing the Tet operon, the minimal CMV promoter, the miR-133 or decoy sequence, and a termination sequence-PolyA was used to generate transgenic mice. We have crossed founders (F0) with mice expressing the reverse tetracycline-responsive transcriptional activator rtTA under the cardiac-specific α-Myosin Heavy Chain (α-MHC) kindly provided by the laboratory of Dr. Wolfgang Dillmann (UCSD).

Figure 5:
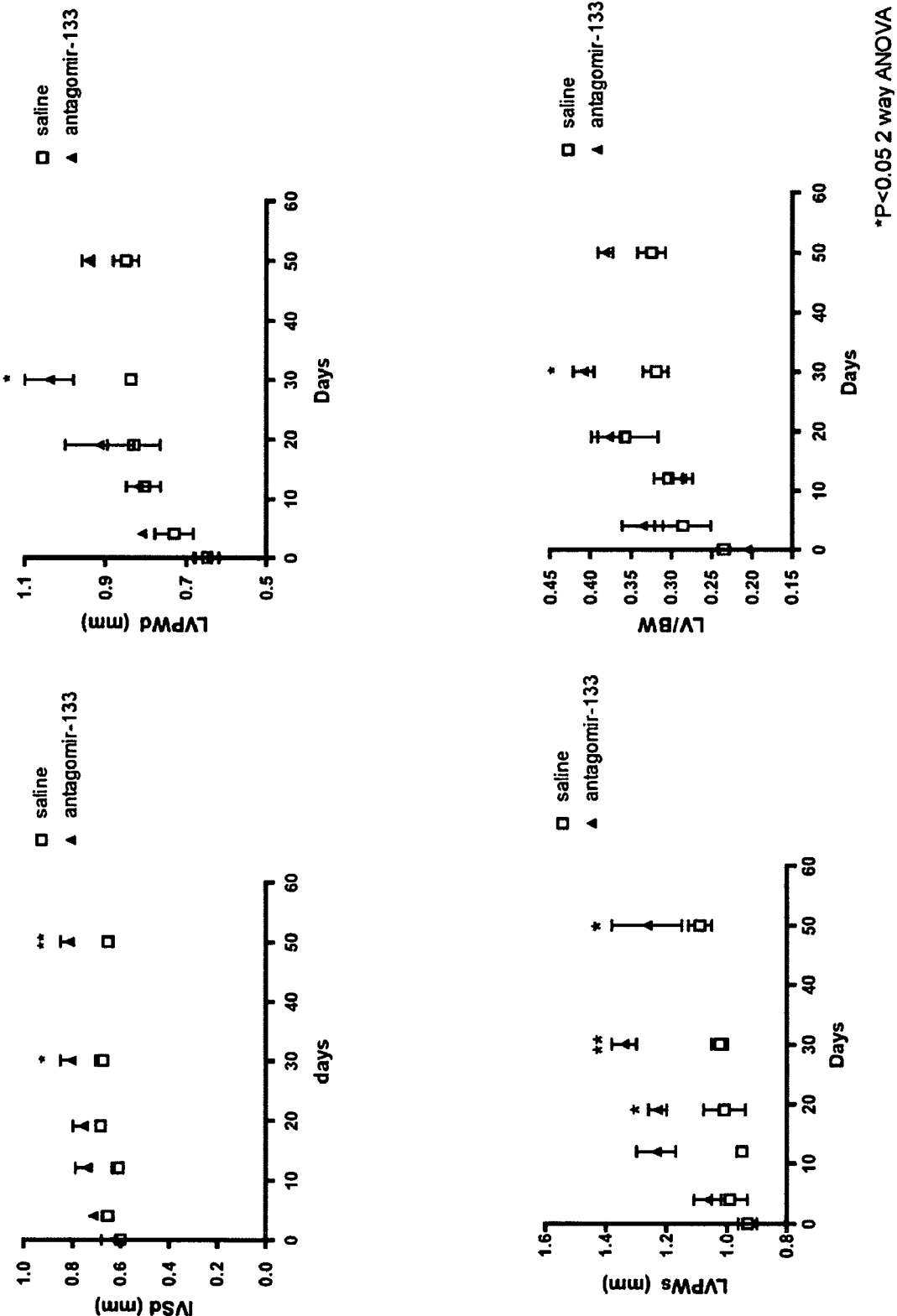

In F1 animals positive for both the decoy-133 operon and rtTA we induced decoy miR-133 under normal, unstressed conditions and checked for the main echocardiographic and morphometric parameters of cardiac hypertrophy. Data show a significant increment of Left Ventricular Diastolic/Systolic Posterior Wall Thickness (LVPWd, LVpWs) and Interventricular Wall Thickness (IVsd), two principal echocardiographic parameters of cardiac hypertrophy (FIG. 5). Left Ventricular Weight to Body Weight (LV/BW) ratio, a gravimetric parameter obtained after sacrifice, was also significantly increased after tetracycline induction of miR133 decoy (FIG. 5). To determine whether miR-1, beside miR-133, is also involved in cardiac hypertrophy in vivo, we performed in vivo experiments using a 3'-cholesterol-conjugated miR-1 antisense molecule named antagomir[33] against miR-1. All the bases were 2'-OMe modified. The antagomir sequence complementary to miR-1 is:

The nucleotide portion is (SEQ. ID NO. 12).

Antagomir oligonucleotides were deprotected, desalted and purified by high-performance liquid chromatography (HPLC; Dharmacon). C57BL/6 female mice (8 weeks old) received antagomirs at doses of 80 mg/kg body weight through Alzet osmotic minipumps (model 1003D, Alza). Minipumps were prepared and placed in a petri dish filled with sterile 0.9% saline at 371 C, for at least 4 h before implantation, in order to prime the pumps for continuous delivery of the drug. Controls received a saline minipump.

Figure 6:
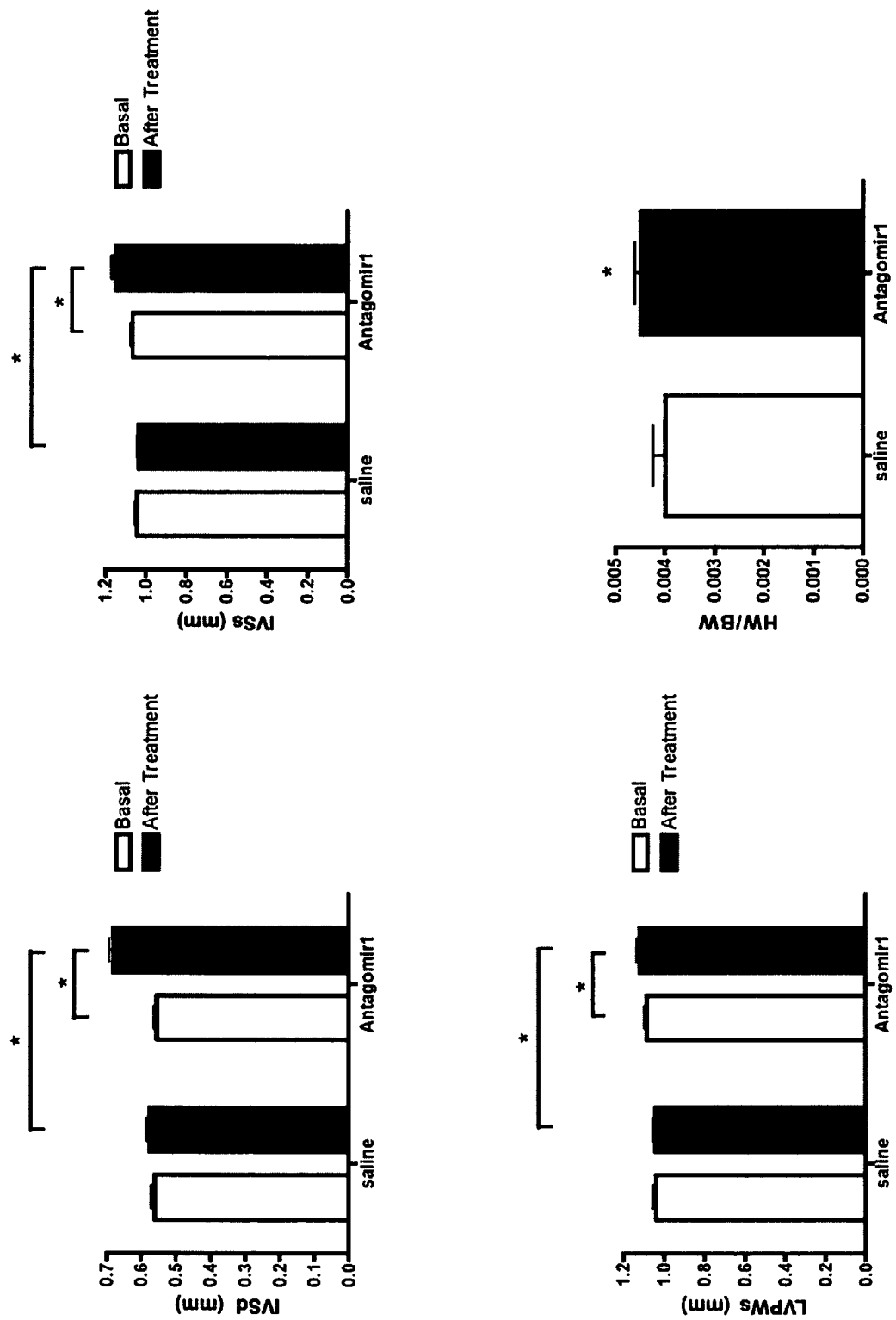

Echocardiographic and morphometric analysis was conducted on mice treated with antagomiR-1 and saline control group (FIG. 6). An analysis conducted after thirty days of treatment revealed a significant increase of IVSd thickness and of LV/BW ratio, together with an increase of parameters of systolic function such as LVPWs and IVSs.

NELF-A and CDC42 are Significant Targets of miR-133.

To identify potential miR target(s) involved in the observed hypertrophy-modulation process, we searched for putative miR target(s) using the software programs TargetScan (http://genes.mit.edu/targetscan/)[1], miRanda, (http://www.microrna.org/)[24] and PicTar, http://pictar.bio.nyu.edu/)[25]. Interestingly, the analysis suggested diverse miR-133 target genes related to heart development and hypertrophy. We focused on NELF-A/WHSC2 and CDC42, whose mRNA 3'UTR regions comprise canonical "seed" sequences and flanking nucleotides matching miR-133 (FIGS. 7, 8, bottom panels). NELF-A, a nuclear molecule interacting with RNA polymerase II and negatively regulating its function[26], is linked to the Wolf-Hirschhorn syndrome, which is characterised by cardiac dysgenesis among multiple abnormalities[27]. CDC42 is a member of the Rho subfamily (RhoA, Rac1, and CDC42) of small GTP-binding proteins, involved in cytoskeleton and myofibrillar re-organisation during cardiac hypertrophy[28]. In isolated rat CMCs, overexpression of activated small GTP-binding proteins, including CDC42, induces various features of hypertrophy[29].

Several lines of evidence indicate that NELF-A and CDC42 are regulated by miR-133 in heart hypertrophy. Specifically, (a) in TAC-treated and Akt Tg mice, miR-133 expression level is inversely related to the amount of the two proteins (FIG. 7a, 8a; see also FIG. 2). Furthermore, (b) in both neonatal and adult CMCs miR-133 over-expression or down-modulation, by infection with AdDecoy or Ad133, causes either an increase or a marked downmodulation of the two proteins respectively, whereas mRNA levels are unmodified (FIG. 7b,c, 8b,c).

These data suggest that NELF-A and CDC42 mRNAs are targeted by miR-133 in CMCs. To test this hypothesis, we performed a luciferase reporter assay in the miR-133-negative 293FT and HeLa cell lines. The 3'UTR regions, inserted downstream of the firefly luciferase gene, were co-transfected with miR-133 or control non-targeting miR. As shown in FIGS. 7d and 8d, the transfection of miR-133 with wild type UTRs of NELF-A and CDC42 induced a significant decrease in luciferase activity. In contrast, cotransfection of NELF-A or CDC42 UTR with control non-targeting miR abolished this repression, thus indicating the specificity of the miR133-UTRs interaction. Since NELF-A 3'UTR comprises two "seed" target sequences (FIG. 7d, SEQ ID NOs: 16 and 17), we also tested two mutated UTRs, each including 6 nucleotide substitutions in a seed sequence (FIG. 12, SEQ ID NOs: 21 and 22). These mutations abolished the repression of luciferase activity, indicating that both seed sequences are necessary to mediate miR-133-induced translation repression. At least four seed target sites are present in the long (1.4 Kb) 3' UTR of CDC42 (two "high score" sites are shown in FIG. 8d, SEQ ID NOs: 18 and 19).

BIBLIOGRAPHY

1. Bartel, D. P. MicroRNAs: genomics, biogenesis, mechanism, and function. *Cell* 116, 281-97 (2004).
2. Lagos-Quintana, M., Rauhut, R., Lendeckel, W., Tuschl, T. Identification of novel genes coding for small expressed RNAs. *Science* 294, 853-858 (2001).
3. Lagos-Quintana, M., Rauhut, R., Meyer, J., Borkhardt, A., Tuschl, T. New microRNA from mouse and human. *RNA* 9, 175-179 (2003).
4. Houbaviy, H. B., Murray, M. F., Sharp, P.A. Embryonic stem cell-specific microRNAs. *Dev. Cell.* 5, 351-358 (2003).
5. Lim, L. P., Glasner, M. E., Yekta, S., Burge, C. B., Bartel, D. P. Vertebrate microRNA genes. *Science* 299, 1540 (2003).
6. Xu, P., Guo, M., Hay, B. A. MicroRNAs and the regulation of cell death. *Trends Genet.* 20, 617-624 (2004).
7. Cheng, A. M., Byrom, M. W., Shelton, J., Ford, L. P. Antisense inhibion of human miRNAs and indications for an involvemente of miRNA in cell growth and apoptosis. *Nucleic Acids Res.* 33, 1290-1297 (2005).
8. Felli, N. et al. MicroRNAs 221 and 222 inhibit normal erythropoiesis and erythroleukemic cell growth via kit receptor down-modulation. *Proc Natl Acad Sci USA* 102, 18081-6 (2005).
9. Chen, C. Z., Li, L., Lodish, H. F., Bartel, D. P. MicroRNAs modulate hematopoietic lineage differentiation. *Science* 303, 83-86 (2004).
10. Xu, P, Vernooy, S. Y., Guo, M., Hay, B. A. The *Drosophila* microRNA Mir-14 suppresses cell death and is required for normal fat metabolism. *Curr Biol* 13, 790-795 (2003).
11. Poy, M. N. et al. A pancreatic islet-specific microRNA regulates insulin secretion. *Nature* 432, 226-230 (2004).
12. Dresios, J., et al. Cold stress-induced protein Rbm3 binds 60S ribosomal subunits, alters microRNA levels, and enhances global protein synthesis. *Proc Natl Acad Sci USA* 102, 165-1870 (2005).
13. Krek, A. et al. Combinatorial microRNA target predictions. *Nature Genet.* 37, 495-500 (2005).
14. Esquela-Kerscher, A. & Slack F. J. Oncomirs-microRNAs with a role in cancer. *Nature Rev. Cancer* 6, 259-269 (2006).
15. Zhao, Y., Samal, E. & Srivastava, D. Serum response factor regulates a muscle-specific microRNA that targets Hand2 during cardiogenesis. *Nature* 436, 214-20 (2005).
16. Kwon, C., Han, Z., Olson, E. N. & Srivastava, D. MicroRNA1 influences cardiac differentiation in *Drosophila* and regulates Notch signaling. *Proc Natl Acad Sci U S A* 102, 18986-91 (2005).
17. McKinsey, T. A., Olson, E. N. Toward transcriptional therapies for the failing heart: chemical screens to modulate genes. *J Clin Invest* 115, 538-546 (2005)
18. Liu, C. G. et al. An oligonucleotide microchip for genome-wide microRNA profiling in human and mouse tissues. *Proc Natl Acad Sci USA* 101, 9740-4 (2004).
19. Condorelli, G. et al. Akt induces enhanced myocardial contractility and cell size in vivo in transgenic mice. *Proc Natl Acad Sci USA* 99, 12333-8 (2002).
20. Dorn, G. W., 2nd, Robbins, J. & Sugden, P. H. Phenotyping hypertrophy: eschew obfuscation. *Circ Res* 92, 1171-5 (2003).
21. Latronico, M. V., Costinean, S., Lavitrano, M. L., Peschle, C. & Condorelli, G. Regulation of cell size and contractile function by AKT in cardiomyocytes. *Ann N Y Acad Sci* 1015, 250-60 (2004).
22. Brown, B. D., Venneri, M. A., Zingale, A., Sergi Sergi, L., Naldini, L. Endogenous microRNA regulation suppresses transgene expression in hematopoietic lineages and enables stable gene transfer. *Nat Dev published* 23 Apr. 2006.
23. Iwatate, M. et al. *Gene Ther* 10, 1814-1820 (2003).
24. John, B. et al. Human MicroRNA targets. *PLoS Biol* 2, e363 (2004).
25. Krek, A. et al. Combinatorial microRNA target predictions. *Nat Genet* 37, 495-500 (2005).

26. Wu, C. H. et al. NELF and DSIF cause promoter proximal pausing on the hsp70 promoter in *Drosophila*. *Genes Dev* 17, 1402-14 (2003).
27. Bergemann, A. D., Cole, F. & Hirschhorn, K. The etiology of Wolf-Hirschhorn syndrome. *Trends Genet* 21, 188-95 (2005).
28. Clerk, A. & Sugden, P. H. Small guanine nucleotide-binding proteins and myocardial hypertrophy. *Circ Res* 86, 1019-23 (2000).
29. Nagai, T. et al. Cdc42 plays a critical role in assembly of sarcomere units in series of cardiac myocytes. *Biochem Biophys Res Commun* 305, 806-10 (2003).
30. Pei, Y., Schwer, B. & Shuman, S. Interactions between fission yeast Cdk9, its cyclin partner Pch1, and mRNA capping enzyme Pct1 suggest an elongation checkpoint for mRNA quality control. *J Biol Chem* 278, 7180-8 (2003).
31. Sano, M. et al. Activation and function of cyclin T-Cdk9 (positive transcription elongation factor-b) in cardiac muscle-cell hypertrophy. *Nat Med* 8, 1310-7 (2002).
32. Chen, J. F. et al. The role of microRNA-1 and microRNA-133 in skeletal muscle proliferation and differentiation. *Nat Genet* 38, 228-33 (2006).
33. Krutzfeldt, J. et al. Silencing of microRNAs in vivo with antagomirs. *Nature* 438, 685-689 (2005).

LEGEND TO FIGURES

FIG. 1. MiR-133 and miR-1 expression in mouse cardiac hypertrophy. (a) Top panel, Northern blot analysis of miR-133 expression using total RNA from sham-operated, transverse aortic arch constricted (TAC) and Akt transgenic mice (representative results); bottom, relative expression values (mean±SD, a minimum of n=5 mice per group) obtained by densitometric analysis. *P<0.05, **P<0.01 when compared to sham. (b) miR-1 expression results, presented as in a.

FIG. 2. Infection of neonatal CMCs with Ad133: inhibition of agonist-induced hypertrophy. (a) Northern blot analysis of miR-133 expression using total RNA from 293 cell line infected with Ad133 (1, control; 2, m.o.i. 1; 3, m.o.i. 50). (b) Hypertrophy level, evaluated as CMC $^3$H-leucine incorporation (mean±SD, a minimum of 3 experiments per group), in neonatal CMCs infected or not with Ad133 (m.o.i. 100) and treated or not with 100 μM phenylephrine (PE) or 100 nM endothelin-1 (ET1). *P<0.01 versus mock, °P<0.01 versus mock+PE or +ET1. (c) Confocal microscopy of mock and Ad133 infected cells immunostained for actin (red) and ANF (green) proteins. (d) Dot blot performed with total RNA extracted from neonatal CMCs. The expression level of "foe-tal" cardiac genes, normalized for GAPDH expression, is evaluated as fold induction over mock cells (mean±SD, a minimum of n=3 experiments per group)*P<0.01 versus mock; $^\Delta$P<0.05, °P<0.01 versus mock+PE.

FIG. 3. Infection of neonatal CMCs with AdDecoy: induction of hypertrophy in the presence or not of phenylephrine (PE). (a) Left panel, CMC $^3$H-leucine incorporation assay (mean±SD, a minimum of 3 experiments per group); right, Northern blot of miR-133. (b) Confocal analysis of mock and AdDecoy infected immunostained for actin (red) and ANF (green) proteins. (d) Dot blot analysis of "fetal" cardiac genes in AdDecoy infected CMCs, evaluated as fold induction over mock control values (mean±SD, a minimum of 3 experiments per group). *P<0.05 and **P<0.01 versus mock; °P<0.01 versus mock+PE. For other details, see FIG. 3 legend.

Figure 4:
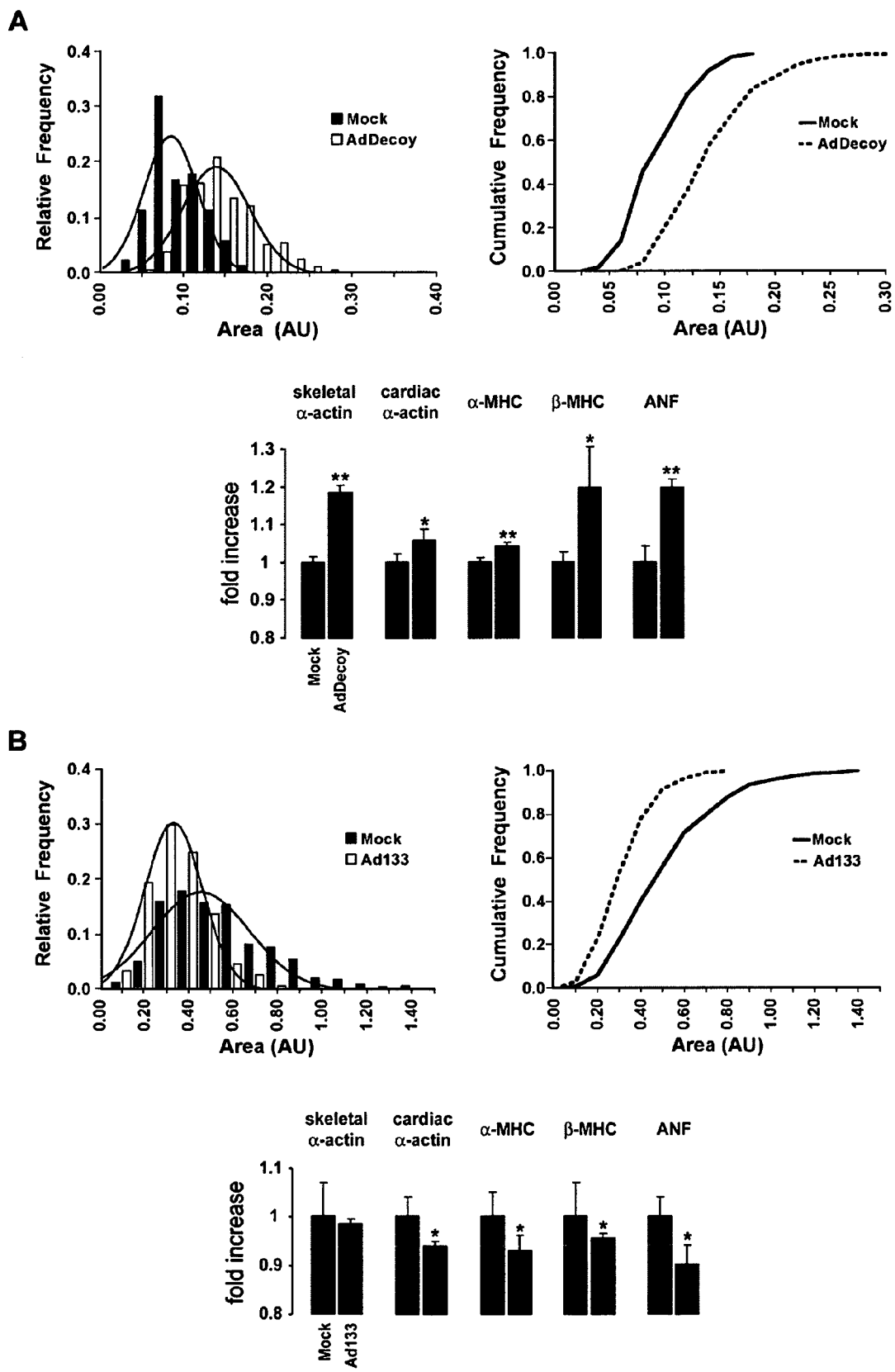

FIG. 4. In vivo effect of AdDecoy and Ad133 on cardiac hypertrophy. (a) Top panels. Relative and cumulative frequency distribution analysis of left ventricle CMCs size after AdDecoy gene transfer in wt mice [n=10 per group]. CMCs were isolated 14 days post gene transfer and cell size analyzed with imageJ (n=400). Values are expressed in terms of arbitrary units, P<0.001 when compared to mock. Bottom panel. Dot blot of total RNA extracted from CMCs (n=4 for each treated group). The expression level of "fetal" cardiac genes, normalized for GAPDH expression, is evaluated as fold induction over mock cells (mean±SD). *P<0.05, **P<0.01 versus mock. (b) Top panels. Left ventricle CMC size after Ad133 gene transfer in Akt Tg mice (n=10). P<0.05 when compared to mock. Bottom. Dot blot of total RNA expression in CMCs (n=4). *P<0.05 versus mock.

FIG. 5. Time course of in vivo effects of decoy-133. *P<0.05, **P<0.01 when compared to Saline group.

FIG. 6. In vivo effects of antagomir-1. *P<0.05 when compared to Saline group.

FIG. 7. Identification of miR-133 target genes: NELF-A. (a) Western blot of NELF-A from sham, Akt Tg and TAC mice. (b) Western (left) and Northern (right) blot of mock, Ad133 and AdDecoy infected 293 cell line. (c) Mock, Ad133 and AdDecoy infected (m.o.i. 200) adult CMCs immunostained for NELF-A expression. (d) Upper panel, NELF-A mRNA 3'UTR sites (SEQ ID NO: 16 and SEQ ID NO:17) targeted by miR-133 (SEQ ID NO: 1). Lower panel, luciferase reporter assays (mean±SD values, a minimum of 5 experiments per group) performed with NELF-A 3'UTR containing either wild type or mutated miR-133 complementary sites cotransfected with the miR-133 oligomer; a control non-targeting oligomer is included. **P<0.01 vs controls; °P<0.05 vs wild type 3' UTR+miR-133.

FIG. 8. Identification of miR-133 target genes: CDC42. (a) Western blot of CDC42 from sham, Akt Tg, and TAC mice. (b) Western (left) and Northern (right) blot from mock, Ad133 and AdDecoy infected 293 cell line. c) Adult CMCs infected with mock, Ad133, and AdDecoy (m.o.i. 200) and immunostained for CDC42 expression. (d) Upper panel, CDC42 mRNA 3'UTR sites (SEQ ID NO:18 and SEQ ID NO: 19) targeted by miR-133 (SEQ ID NO:1). Lower panel, luciferase reporter assays (mean±SD values, a minimum of 4 experiments per group), performed with wild type CDC42 3'UTR, cotransfected with miR-133 oligomer; a non-targeting oligomer is included as control. **P<0.01 versus controls.

TABLE 1

Echocardiographic assessment in WT and E40Tg mice in basal condition and after pressure overload stimuli

|  | WT (n = 6) Sham | WT (n = 7) 1 week TAC | Akt (N = 5) Sham |
|---|---|---|---|
| BW(g) | 23.1 ± 2.3 | 20.8 ± 2.9 | 25.6 ± 0.9 |
| H/BW | 0.44 ± 0.055 | 0.6210 ± 0.054* | 0.745 ± 0.12† |
| HR | 422 ± 29 | 432 ± 19 | 446 ± 10 |
| IVSd | 0.56 ± 0.08 | 0.6 ± 0.06* | 0.7 ± 0.05† |
| LVEDD | 2.48 ± 0.18 | 2.6 ± 0.19 | 3.1 ± 0.5†† |
| LVPWd | 0.662 ± 0.05 | 0.8 ± 0.08** | 0.8 ± 0.06† |
| IVSs | 0.754 ± 0.07 | 1.1 ± 0.07* | 1.2 ± 0.1† |
| LVESD | 1.388 ± 0.1 | 1.2 ± 0.14 | 1.5 ± 0.16 |
| LVPWs | 0.702 ± 0.08 | 1 ± 0.09* | 1.11 ± 0.47† |
| % FS | 44 ± 0.98 | 52 ± 4* | 50 ± 3.4† |
| VCF | 6.2 ± 0.87 | 7.7 ± 1.14** | 7.5 ± 0.85 |

Values are expressed as mean ± SD.
BW, body weight;
HW, heart weight;
LVEDD, left ventricle end-diastolic diameter;
LVESD, left ventricle end-systolic diameter;
IVSd/s, interventricular sept thickness in diastole/systole;
LVPWd/s, left ventricle posterior wall thickness in diastole/systole;
FS, fractional shortening;
VCF, velocity of circumferential fiber shortening calculated as FS divided by ejection time multiplied by square root of RR interval.
*/**P < 0.001, <0.01 when comparing TAC vs respective sham wild-type
†/††P < 0.001, <0.01 when comparing sham E40K Tg mice vs wilde-type mice

TABLE 2

Post-mortem heart weight data of WT and E40Tg mice in basal condition and after pressure overload stimuli

|  | WT (n = 6) Sham | WT (n = 7) 1 week TAC | Akt (N = 5) Sham |
|---|---|---|---|
| BW (g) | 23.1 ± 2.3 | 20.8 ± 2.9 | 25.6 ± 0.9† |
| LV (g) | 0.0802 ± 0.007 | 0.0988 ± 0.0144* | 0.133 ± 0.033† |
| RV (g) | 0.0159 ± 0.003 | 0.017 ± 0.0023 | 0.0316 ± 0.0047† |
| LA (g) | 0.003 ± 0.0012 | 0.0044 ± 0.0008* | 0.0091 ± 0.0063†† |
| RA (g) | 0.003 ± 0.0004 | 0.0036 ± 0.0009 | 0.0174 ± 0.011†† |
| HW (g) | 0.1020 ± 0.009 | 0.1238 ± 0.0161* | 0.191 ± 0.036† |
| LV/BW | 0.34 ± 0.037 | 0.4986 ± 0.051* | 0.51 ± 0.113† |
| HW/BW | 0.44 ± 0.055 | 0.6210 ± 0.054 | 0.745 ± 0.12† |

Values are expressed as mean ± SD.
BW, body weight;
LV, left ventricle;
RV, right ventricle;
LA, left atrium;
RA, right atrium;
HW, heart weight.
*/**P < 0.001, <0.01 when comparing TAC vs respective sham wild-type
†/††P < 0.001, <0.01 when comparing sham E40K Tg mice vs wilde-type mice Legend to FIGS. 9-12

Figure 9:
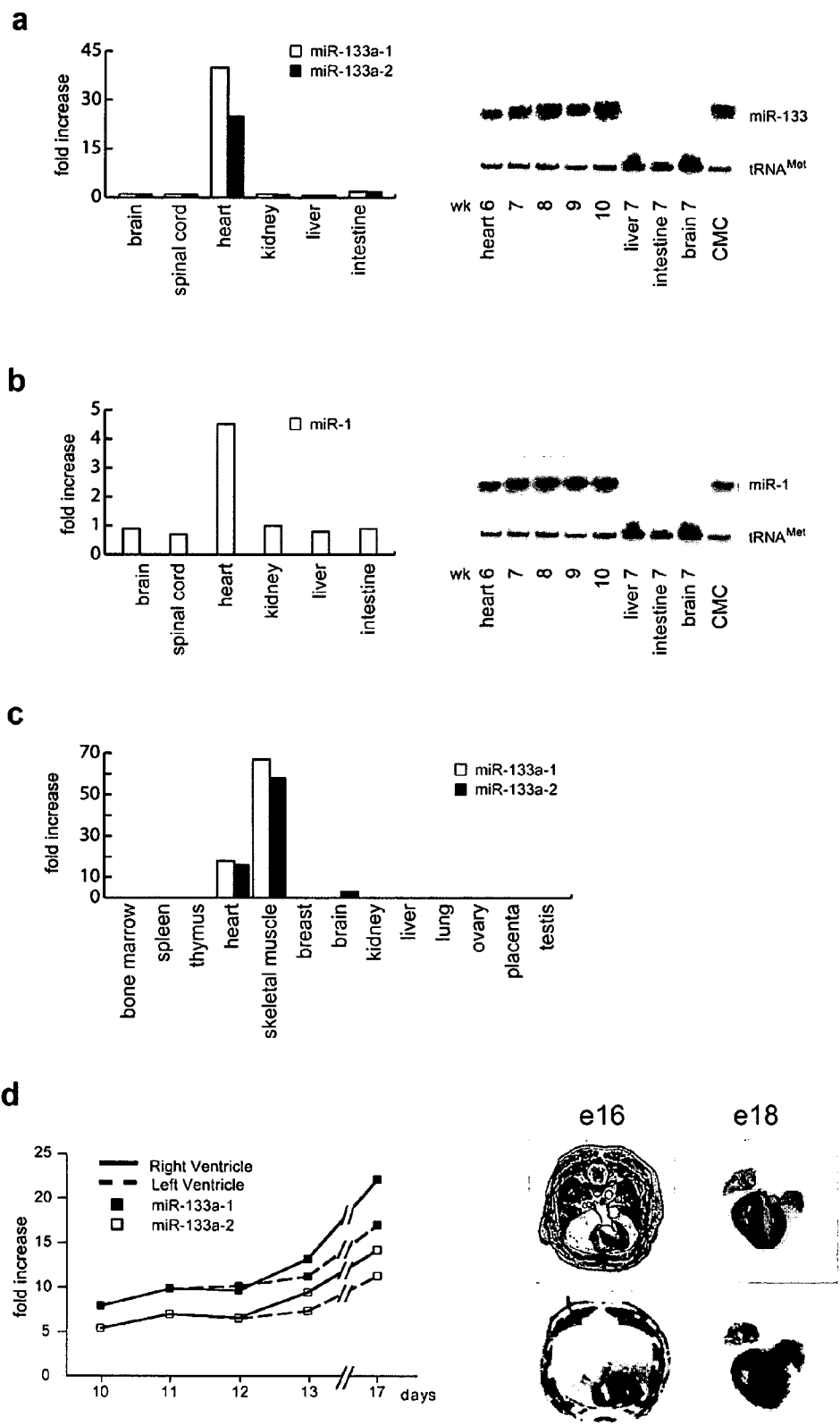

FIG. 9 miR-133 and miR-1 expression in fetal and adult tissues. (a,b) Relative expression of miR-133 and miR-1, evaluated by a microarray chip including the human miR-133-a-1/a-2 and miR-1-1/-2 precursors isoforms, in human 7-wk embryonic tissues (left panels); results were confirmed by Northern blot (right panels). (c) microarray analysis of miR-133 expression in adult murine tissues. (d) left panel, microarray analysis of miR-133 expression in murine heart during embryonic development; right panels, in situ hybridization performed on day 16 and day 18 of murine development (left, thorax sagittal section; right, heart section. Toluidine blue staining and miR-133 probing in the upper and lower panels respectively). Microarray results are expressed in terms of fold increase over median values. CMC, cardiomyocyte.

FIG. 10 Upper panel, structure of the AdDecoy including SEQ ID NO: 20 containing tandem "decoy" sequences complementary to miR-133a (SEQ ID No:3) indicated in red. Lower panel: Neonatal CMCs were mock and AdDecoy (m.o.i. 200) infected. 3 h post infection 100 µM Pheylephrine was added. 24 h later GFP expression was evaluated.

FIG. 11 Morphological analysis of mock (A), Ad133 (B) or AdDecoy (C) infected adult CMCs (m.o.i. 200), evaluated at 48 h after infection (mean±SD values). At least 300 CMCs were randomly selected per each group. ** $P<0.01$, * $P<0.05$ when compared to mock. Values are expressed in terms of arbitrary units.

FIG. 12 Mutations of 3'UTR NELF-A "seed" sequences. "Seed" sequences are SEQ ID NO: 21 (Seed 1) and SEQ ID NO: 22 (Seed 2).

The invention claimed is:

1. A method for treatment of cardiac disease which comprises the step of administering to an individual in need of treatment a medicament an RNA selected from the group consisting of SEQ ID NO. 1 and SEQ ID NO. 15.

2. The method according to claim 1, wherein the RNA is capable of binding to NELF-A and CDC-42 mRNAs.

3. The method according to claim 1, wherein the RNA is provided in the form of a primary transcript.

4. The method according to claim 1, wherein the RNA consists of SEQ. ID NO. 1.

5. The method according to claim 1, wherein the medicament comprises a vector suitable to introduce the RNA into cardiac myocyte cells.

6. The method according to claim 1, wherein the medicament comprises a vector containing a nucleic acid sequence coding for RNA as defined, and wherein said vector is suitable to transform cardiac myocyte cells with said coding nucleic acid sequence.

7. The method according to claim 6, wherein the nucleic acid sequence is DNA.

8. The method according to claim 6, wherein the nucleic acid sequence is RNA.

9. The method of claim 1 wherein the cardiac disease is cardiac myocyte cell hypertrophy.

10. The method according to claim 1, wherein the RNA consists of SEQ. ID NO. 15.

* * * * *

```
                        SEQUENCE LISTING

<160> NUMBER OF SEQ ID NOS: 22

<210> SEQ ID NO 1
<211> LENGTH: 22
<212> TYPE: RNA
<213> ORGANISM: Homo sapiens

<400> SEQUENCE: 1
uugguccccu ucaaccagcu gu                                            22

<210> SEQ ID NO 2
<211> LENGTH: 21
<212> TYPE: RNA
<213> ORGANISM: Homo sapiens

<400> SEQUENCE: 2
uggaauguaa agaaguaugu a                                             21

<210> SEQ ID NO 3
<211> LENGTH: 22
<212> TYPE: DNA
<213> ORGANISM: artificial
<220> FEATURE:
<223> OTHER INFORMATION: probe

<400> SEQUENCE: 3
acagctggtt gaaggggacc aa                                            22

<210> SEQ ID NO 4
<211> LENGTH: 18
<212> TYPE: DNA
<213> ORGANISM: artificial
<220> FEATURE:
<223> OTHER INFORMATION: probe

<400> SEQUENCE: 4
```
tacatacttt acattcca                                                  18

<210> SEQ ID NO 5
<211> LENGTH: 36
<212> TYPE: DNA
<213> ORGANISM: artificial
<220> FEATURE:
<223> OTHER INFORMATION: probe

<400> SEQUENCE: 5
tggtagcaga ggatggtttc gatccatcga cctctg                              36

<210> SEQ ID NO 6
<211> LENGTH: 60
<212> TYPE: DNA
<213> ORGANISM: artificial
<220> FEATURE:
<223> OTHER INFORMATION: probe

<400> SEQUENCE: 6
aatgtgacca agctgcgtga cacaccacaa gggcttagga tcttttgcga tctgctcaag    60

<210> SEQ ID NO 7
<211> LENGTH: 59
<212> TYPE: DNA
<213> ORGANISM: artificial
<220> FEATURE:
<223> OTHER INFORMATION: probe

<400> SEQUENCE: 7
tgtacaatga ctgatgagag atggggaggg ggctcagagg attccaagaa gcacaatac     59

<210> SEQ ID NO 8
<211> LENGTH: 60
<212> TYPE: DNA
<213> ORGANISM: artificial
<220> FEATURE:
<223> OTHER INFORMATION: probe

<400> SEQUENCE: 8
tggagcaaaa cagaatggct ggctttaatg cttcaagttt tccatttcct ttccacaggg    60

<210> SEQ ID NO 9
<211> LENGTH: 50
<212> TYPE: DNA
<213> ORGANISM: artificial
<220> FEATURE:
<223> OTHER INFORMATION: probe

<400> SEQUENCE: 9
cgaacgttat gtttattgtg tattggccac agcgaagggt ctgctgagag               50

<210> SEQ ID NO 10
<211> LENGTH: 57
<212> TYPE: DNA
<213> ORGANISM: artificial
<220> FEATURE:
<223> OTHER INFORMATION: probe

<400> SEQUENCE: 10
gctttattct gcttccacct aaagggctgt tgcaaaggct ccaggtctga gggcttc       57

<210> SEQ ID NO 11
<211> LENGTH: 35
<212> TYPE: DNA
<213> ORGANISM: artificial
<220> FEATURE:

```
<223> OTHER INFORMATION: probe

<400> SEQUENCE: 11
ggaacatgta gaccatgtag ttgaggtcaa tgaag                              35

<210> SEQ ID NO 12
<211> LENGTH: 21
<212> TYPE: RNA
<213> ORGANISM: artificial
<220> FEATURE:
<223> OTHER INFORMATION: antagomir sequence complementary to miR-1

<400> SEQUENCE: 12
uacauacuuc uuuacauucc a                                            21

<210> SEQ ID NO 13
<211> LENGTH: 21
<212> TYPE: RNA
<213> ORGANISM: artificial
<220> FEATURE:
<223> OTHER INFORMATION: antagomir of miR 133

<400> SEQUENCE: 13
acagcugguu gaagggggaca a                                           21

<210> SEQ ID NO 14
<211> LENGTH: 21
<212> TYPE: RNA
<213> ORGANISM: artificial
<220> FEATURE:
<223> OTHER INFORMATION: antagomir of miR 1

<400> SEQUENCE: 14
uacauacuuc uuuacauucc a                                            21

<210> SEQ ID NO 15
<211> LENGTH: 21
<212> TYPE: RNA
<213> ORGANISM: Homo sapiens

<400> SEQUENCE: 15 uuggucccu ucaaccagcu a                                             21

<210> SEQ ID NO 16
<211> LENGTH: 34
<212> TYPE: RNA
<213> ORGANISM: Homo sapiens

<400> SEQUENCE: 16
acagcuggaa agucuagggu gugagggggg cuau                              34

<210> SEQ ID NO 17
<211> LENGTH: 21
<212> TYPE: RNA
<213> ORGANISM: Homo sapiens

<400> SEQUENCE: 17
ucaugagguu gaggggacca a                                            21

<210> SEQ ID NO 18
<211> LENGTH: 22
<212> TYPE: RNA
<213> ORGANISM: Homo sapiens

<400> SEQUENCE: 18
```

-continued

```
ccugauuuag ggagggggaau aa                                         22

<210> SEQ ID NO 19
<211> LENGTH: 22
<212> TYPE: RNA
<213> ORGANISM: Homo sapiens

<400> SEQUENCE: 19
augagcaugg ggugggagc au                                           22

<210> SEQ ID NO 20
<211> LENGTH: 62
<212> TYPE: DNA
<213> ORGANISM: artificial
<220> FEATURE:
<223> OTHER INFORMATION: vector sequence-AdDecoy

<400> SEQUENCE: 20
acagctggtt gaaggggacc aaagagaact tagagaactt acagctggtt gaaggggacc  60
aa                                                                62

<210> SEQ ID NO 21
<211> LENGTH: 37
<212> TYPE: DNA
<213> ORGANISM: homo sapiens

<400> SEQUENCE: 21
agtctagggt gtgagggggg ctatgaccag ccttgat                          37

<210> SEQ ID NO 22
<211> LENGTH: 37
<212> TYPE: DNA
<213> ORGANISM: Homo sapiens

<400> SEQUENCE: 22
cctcatgagg ttgagggggac caaaggtgac agctgga                         37
```